(12) United States Patent
Kawano et al.

(10) Patent No.: US 10,261,050 B2
(45) Date of Patent: Apr. 16, 2019

(54) METHOD FOR MEASURING CHARACTERISTICS OF A PARTICLE AND DEVICE FOR MEASURING CHARACTERISTICS OF A PARTICLE

(71) Applicant: OSAKA UNIVERSITY, Osaka (JP)

(72) Inventors: Makoto Kawano, Suita (JP); Hitoshi Watarai, Suita (JP); Nobutoshi Ota, Suita (JP)

(73) Assignee: OSAKA UNIVERSITY, Osaka (JP)

( * ) Notice: Subject to any disclaimer, the term of this patent is extended or adjusted under 35 U.S.C. 154(b) by 191 days.

(21) Appl. No.: 14/915,062

(22) PCT Filed: Aug. 29, 2014

(86) PCT No.: PCT/JP2014/072761
§ 371 (c)(1),
(2) Date: Feb. 26, 2016

(87) PCT Pub. No.: WO2015/030184
PCT Pub. Date: Mar. 5, 2015

(65) Prior Publication Data
US 2016/0209366 A1 Jul. 21, 2016

(30) Foreign Application Priority Data

Aug. 30, 2013 (JP) .................................. 2013-179145

(51) Int. Cl.
*G01N 27/76* (2006.01)
*G01N 15/10* (2006.01)
*G01N 15/08* (2006.01)

(52) U.S. Cl.
CPC ........... *G01N 27/76* (2013.01); *G01N 15/088* (2013.01); *G01N 15/1031* (2013.01)

(58) Field of Classification Search
CPC ... G01N 27/76; G01N 15/1031; G01N 15/088
(Continued)

(56) References Cited

U.S. PATENT DOCUMENTS 4,489,593 A * 12/1984 Pieters ............... G01N 15/0893
73/38
5,408,864 A 4/1995 Wenman
(Continued)

FOREIGN PATENT DOCUMENTS

JP 2002-071645 A 3/2002
JP 2002-357594 A 12/2002
(Continued)

OTHER PUBLICATIONS

Extended European Search Report (EESR) dated Apr. 11, 2017 from corresponding EP Appl No. 14841170.5, 8 pp.
M. Suwa et al., "Magnetoanalysis of micro/nanoparticles: A review," Analytica Chimica Acta, vol. 690, No. 2, Amsterdam, NL, pp. 137-147.
(Continued)

*Primary Examiner* — Daniel S Larkin
*Assistant Examiner* — Anthony W Megna Fuentes
(74) *Attorney, Agent, or Firm* — Studebaker & Brackett PC

(57) ABSTRACT

A calculation unit (40) obtains the volume magnetic susceptibility of a first particle. Also, the calculation unit (40) obtains the volume magnetic susceptibility of a second particle different from the first particle. Thereafter, the calculation unit (40) obtains a volume occupied by a surface material included in the second particle on the basis of a relationship between the volume magnetic susceptibility of the first particle, the volume of the first particle, the volume magnetic susceptibility of the second particle, the volume of the second particle, the volume occupied by the surface material, and the volume magnetic susceptibility of the surface material.

14 Claims, 10 Drawing Sheets

(58) Field of Classification Search
USPC .................... 73/865.5, 866, 61.71, 61.72
See application file for complete search history.

(56) References Cited

U.S. PATENT DOCUMENTS

| | | | |
|---|---|---|---|
| 6,825,655 B2 | 11/2004 | Minchole et al. | |
| 2003/0076087 A1 | 4/2003 | Minchole et al. | |
| 2003/0169032 A1 | 9/2003 | Minchole et al. | |
| 2008/0217525 A1* | 9/2008 | Watarai ............... | G01N 27/72 250/282 |
| 2014/0174157 A1 | 6/2014 | Kawano et al. | |

FOREIGN PATENT DOCUMENTS

| | | |
|---|---|---|
| JP | 2004-138464 A | 5/2004 |
| JP | 2005-527782 A | 9/2005 |
| JP | 4318183 B2 | 8/2009 |
| JP | 4599538 B2 | 12/2010 |
| WO | 2013/021910 A1 | 2/2013 |

OTHER PUBLICATIONS

E. Suito et al., "Surface Area Measurement of Powders by Adsorption in Liquid Phase. (I): Calculation of Specific Surface Area of Calcium Carbonate Powders from the Adsorption of Stearic Acid," Bulletin of the Institute for Chemical Research, Kyoto University, vol. 33, No. 1, pp. 1-7.

International Search Report—PCT/JP2014/072761 dated Dec. 2, 2014.

Kawano et al.; Study on the analytical method for the single micro particle by the magnetic; The Magneto-Science Society of Japan Nenkai Yoshishu; Nov. 20, 2012; pp. 123-124.

Suwa et al.; Magnetophoretic Measurements of Interfacial Magnetic Susceptibility of Micro-Organic Droplet; J. Ion Exchange; 2010; vol. 21, No. 1; pp. 41-47.

Fuh et al.; Particle magnetic susceptibility determination using analytical split-flow thin fractionation; Journal of Chromatography A; 2001; pp. 263-270.

Pamme et al.; On-Chip Free-Flow Magnetophoresis: Continuous Flow Separation of Magnetic Particles and Agglomerates; Analytical Chemistry; Dec. 15, 2004; vol. 76, No. 24; pp. 7250-7256.

* cited by examiner

METHOD FOR MEASURING CHARACTERISTICS OF A PARTICLE AND DEVICE FOR MEASURING CHARACTERISTICS OF A PARTICLE

TECHNICAL FIELD

The present invention relates to a particle analysis method and a particle analysis device for analyzing a dispersoid (e.g., particles) on a particle-by-particle basis using the volume magnetic susceptibility.

BACKGROUND ART

Improvements in particle production technologies have recently been accompanied by advances in the attempt to enhance the functions of particles. Therefore, there has been a demand for a technique for accurately evaluating particles in industrial fields.

Particles are employed in a variety of fields. For example, particles are used in many products that are seen in everyday life, such as battery materials, cosmetics, pharmaceutical products, rubber, resins, food additives, paint, and pigments. However, particle evaluation technology has not yet been much advanced.

For example, the surfaces of silica gel particles that are widely used as a dispersant are chemically modified in various manners. Specifically, the surfaces of the silica gel particles are modified by modifier molecules. The modifier molecules impart functions, such as hydrophobicity and the like, to the silica gel particles. The surface-modified particles are evaluated by elementary analysis by microscopic Raman spectroscopy or elementary analysis by electron microscopy. However, in these evaluation methods, it takes a very long time to complete one measurement. For example, it takes about one hour to measure a single particle.

Therefore, the elementary analysis by microscopic Raman spectroscopy or electron microscopy has not been applicable to quality control or the like in industrial fields. In industrial fields, it is necessary to analyze a large number of samples. In addition, the elementary analysis by microscopic Raman spectroscopy or electron microscope cannot be used to measure important aspects, such as surface coverage rate of modifier molecules and the like. The surface coverage rate of modifier molecules refers to the proportion of an area occupied by the modifier molecules to the surface area of a particle. Also, none of the surface area of a particle, the diameter of a pore formed in a particle, and the like, which are other aspects of a particle to be evaluated, can be measured by the elementary analysis by microscopic Raman spectroscopy or electron microscope.

The surface area of a particle and the diameter of a pore formed in a particle, are typically measured using the mercury intrusion technique or the Brunauer-Emmett-Teller (BET) technique. In the BET technique, inert gas, such as nitrogen gas or the like, is used. However, neither the mercury intrusion technique nor the BET technique can be used to measure particles in a solution. Therefore, neither the mercury intrusion technique nor the BET technique can be used to accurately determine the surface area or the like of polymer particles that swell in a solution, in a solution that is an environment where the particles are actually used. Moreover, neither the mercury intrusion technique nor the BET technique can be used to measure particles individually.

The surface coverage rate of modifier molecules can be determined on the basis of the amount of reaction of the modifier molecules. The amount of reaction of modifier molecules is estimated by comparing the amount of modifier molecules that have been used to modify the particle surfaces with the amount of modifier molecules that have remained as residue. However, the measurement method cannot be used to sufficiently evaluate variations in the surface coverage rate. Therefore, it is difficult to accurately measure the surface coverage rate.

Meanwhile, the present inventors have proposed a porosity measuring device (Patent Literature 1). The porosity measuring device is used to measure the porosities of individual particles of a dispersoid dispersed in a dispersion medium and the volumes of the void space of the individual particles of the dispersoid, using the volume magnetic susceptibility (magnetic susceptibility per unit volume). In the porosity measuring device, the dispersion medium may be liquid or gas. Also, the particle may be, for example, a fine particle or a cell.

CITATION LIST

Patent Literature

[Patent Literature 1]
International Publication WO 2013/021910

SUMMARY OF INVENTION

Technical Problem

The present inventors have found a novel technique based on volume magnetic susceptibility. This novel technique can be used to measure a volume that is occupied by a material covering the surface of a particle. The present inventors have also found a technique enabling measurement of the surface area of a particle, the average diameter of pores formed in the particle, the average depth of the pores, the average volume of the pores, and the number of the pores, on the basis of a volume that is occupied by a material covering the surface of the particle. Moreover, the present inventors have found a technique enabling measurement of the surface coverage rate of modifier molecules for a particle using the above novel techniques.

It is an object of the present invention to provide a particle analysis method and a particle analysis device capable of measuring a volume that is occupied by a material covering the surface of a particle.

It is another object of the present invention to provide a particle analysis method and a particle analysis device capable of measuring the surface area of a particle, the average diameter of pores formed in the particle, the average depth of the pores, the average volume of the pores, and the number of the pores.

It is still another object of the present invention to provide a particle analysis method and a particle analysis device capable of measuring the surface coverage rate of modifier molecules for a particle.

Solution to Problem

A particle analysis method according to the present invention may include:
obtaining the volume magnetic susceptibility of a first particle;
obtaining the volume magnetic susceptibility of a second particle different from the first particle; and obtaining a volume occupied by a surface material included in the second particle on the basis of a relationship between the volume magnetic susceptibility of the first particle, the volume of the first particle, the volume magnetic susceptibility of the second particle, the volume of the second particle, the volume occupied by the surface material, and the volume magnetic susceptibility of the surface material.

In the particle analysis method of the present invention, the obtaining the volume magnetic susceptibility of the first particle may include measuring a motion of the first particle in a first dispersion medium in the presence of a magnetic field generated in the first dispersion medium, obtaining a magnetophoretic velocity of the first particle from a result of the measurement of the motion of the first particle, and obtaining the volume magnetic susceptibility of the first particle from the magnetophoretic velocity of the first particle, and the obtaining the volume magnetic susceptibility of the second particle may include measuring a motion of the second particle in a second dispersion medium in the presence of a magnetic field generated in the second dispersion medium, obtaining a magnetophoretic velocity of the second particle from a result of the measurement of the motion of the second particle, and obtaining the volume magnetic susceptibility of the second particle from the magnetophoretic velocity of the second particle.

The particle analysis method of the present invention may further include obtaining the surface area of the first particle by dividing the volume occupied by the surface material by the molecular length of surface molecules included in the surface material.

The particle analysis method of the present invention may further include:

obtaining the surface area of the first particle by dividing the volume occupied by the surface material by the molecular length of surface molecules included in the surface material;

obtaining the porosity of the first particle on the basis of a relationship between the volume magnetic susceptibility of the first particle, the volume magnetic susceptibility of the body of the first particle, and the volume magnetic susceptibility of the first dispersion medium;

obtaining the volume of the void space of the first particle on the basis of a relationship between the porosity, the volume of the void space of the first particle, and the volume of the first particle; and obtaining the average diameter of pores formed in the first particle on the basis of the ratio between the volume of the void space of the first particle and the surface area of the first particle.

The particle analysis method of the present invention may further include obtaining the average depth of the pores on the basis of a relationship between the volume of the void space of the first particle, the volume occupied by the surface material, the average diameter of the pores, and the molecular length of the surface molecules.

The particle analysis method of the present invention may further include obtaining the average volume of the pores on the basis of the average diameter of the pores and the average depth of the pores.

The particle analysis method of the present invention may further include obtaining the number of the pores formed in the first particle on the basis of the volume of the void space of the first particle and the average volume of the pores.

The particle analysis method of the present invention may further include:

obtaining the number of the surface molecules included in the surface material on the basis of the volume occupied by the surface material, the density of the surface molecules, the molecular weight of the surface molecules, and the Avogadro constant; and obtaining an area occupied by the surface molecules on the basis of the number of the surface molecules and the cross-sectional area of each of the surface molecules to obtain the proportion of the area occupied by the surface molecules to the surface area of the first particle.

In the particle analysis method of the present invention the second particle may include the first particle and the surface material covering the surface of the first particle.

A particle analysis device according to the present invention may include a calculation unit, wherein the calculation unit may obtain the volume magnetic susceptibility of a first particle, obtain the volume magnetic susceptibility of a second particle different from the first particle, and obtain a volume occupied by a surface material included in the second particle on the basis of a relationship between the volume magnetic susceptibility of the first particle, the volume of the first particle, the volume magnetic susceptibility of the second particle, the volume of the second particle, the volume occupied by the surface material, and the volume magnetic susceptibility of the surface material.

The particle analysis device of the present invention may further include:

a magnetic field generation unit configured to generate a magnetic field; and a particle measurement unit configured to measure a motion of a particle in a dispersion medium in the presence of a magnetic field generated by the magnetic field generation unit in the dispersion medium, wherein the particle measurement unit may measure a motion of the first particle and a motion of the second particle, and the calculation unit may obtain a magnetophoretic velocity of the first particle from a result of the measurement of the motion of the first particle, obtain the volume magnetic susceptibility of the first particle from the magnetophoretic velocity of the first particle, obtain a magnetophoretic velocity of the second particle from a result of the measurement of the motion of the second particle, and obtain the volume magnetic susceptibility of the second particle from the magnetophoretic velocity of the second particle.

In the particle analysis device of the present invention, the second particle may include the first particle and the surface material covering the surface of the first particle.

Advantageous Effects of Invention

According to the present invention, a volume that is occupied by a material covering the surfaces of individual particles can be measured. Also, according to the present invention, the surface area of a particle, the average diameter of pores formed in the particle, the average depth of the pores, the average volume of the pores, and the number of the pores can be measured. Also, according to the present invention, the surface coverage rate of modifier molecules can be measured for individual particles of a dispersoid.

DESCRIPTION OF EMBODIMENTS

Embodiments of a particle analysis method and a particle analysis device according to the present invention will now be described with reference to FIGS. 1-16. The present invention is not intended to be limited to the embodiments described below and configurations shown in the accompanying drawings, and encompasses equivalents thereof.

[Basic Configuration of Particle Analysis Device]

Figure 1:
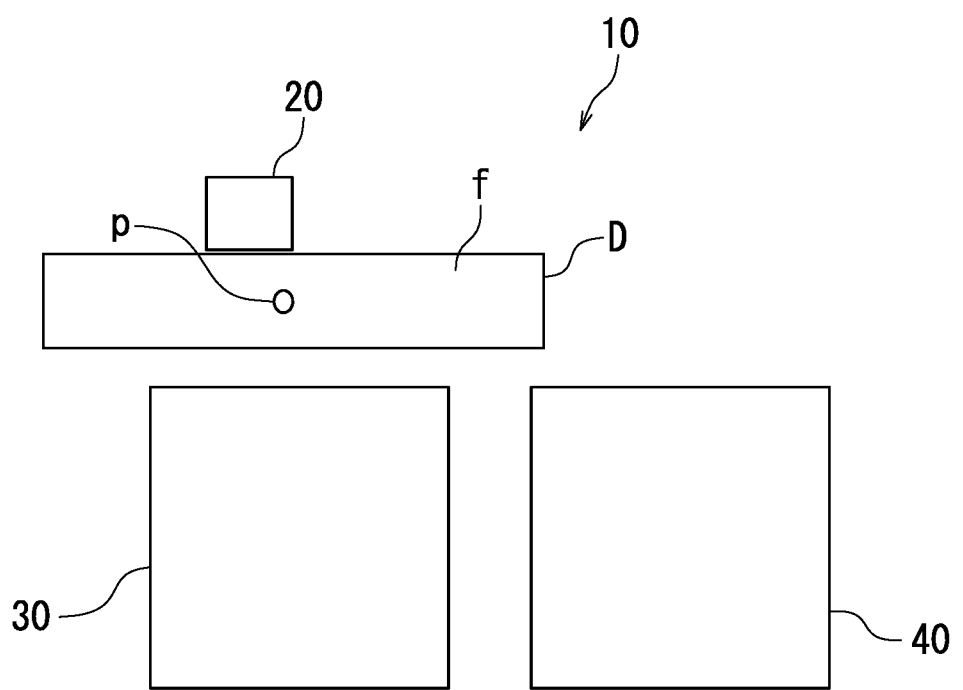
FIG. 1 is a schematic diagram of a particle analysis device according to an embodiment of the present invention.

FIG. 1 is a schematic diagram of a particle analysis device 10 according to this embodiment. The particle analysis device 10 includes a magnetic field generation unit 20, a particle measurement unit 30, and a calculation unit 40. A dispersion system D including a dispersion medium f and a particle p present therein is provided in the vicinity of the magnetic field generation unit 20. The dispersion system D is contained in, for example, a tube-like member. When the magnetic field generation unit 20 generates a magnetic field in the dispersion system D, the particle p moves in a predetermined direction. Such a phenomenon is called magnetophoresis. The magnetic field generation unit 20 includes a superconducting magnet, a magnetic circuit, a permanent magnet, or the like.

The particle measurement unit 30 measures a motion of the particle p in the dispersion medium f in the presence of a magnetic field generated by the magnetic field generation unit 20 in the dispersion system D. Note that, in the description that follows, the particle measurement unit 30 is simply referred to as the measurement unit 30.

Although FIG. 1 shows a situation where a single particle p is present in the dispersion medium f, a plurality of particles p may be present in the dispersion medium f. The dispersion medium f may be liquid or gas. For example, the dispersion medium f may be acetone or acetonitrile. Alternatively, the dispersion medium f may be methanol or water. Alternatively, the dispersion medium f may be, for example, air. The particle p may be a fine particle. Alternatively, the particle p may be a cell (e.g., erythrocyte). The particle p has a diameter of 10 nm or more, preferably between 100 nm and 100 μm.

When the specific gravity of the particle p is at least two times as high as the specific gravity of the dispersion medium f, the particle p settles relatively quickly. In this case, it is preferable that the dispersion medium f be changed to one that has a relatively high specific gravity, or the dispersion medium f be forced to flow using a pump or the like. It is also preferable that the dispersion system D be arranged to extend in the vertical direction, and a change in fall velocity of the particle p due to a magnetic field be measured. In this case, the direction in which the dispersion system D extends is the same as the direction of magnetophoresis performed by the magnetic field generation unit 20. Note that the dispersion medium f may be forced to flow using a pump or the like and the dispersion system D is arranged to extend in the vertical direction.

The particle p and the dispersion medium f have different volume magnetic susceptibilities, which allows the particle p to move in a predetermined direction due to a generated magnetic field. The movement of the particle p varies depending on the magnitude of the magnetic field.

The calculation unit 40 can obtain the surface area of the particle p, the porosity of the particle p, the volume of the void space of the particle p, the average diameter of pores formed in the particle p, the average depth of pores formed in the particle p, the average volume of pores formed in the particle p, and the number of pores formed in the particle p. Prior to obtaining these values, the calculation unit 40 obtains a volume that is occupied by a surface material covering the surface of the particle p. Also, when the surface of the particle p is modified by modifier molecules, the calculation unit 40 can obtain the surface coverage rate of the modifier molecules. Prior to obtaining the surface coverage rate of the modifier molecules, the calculation unit 40 obtains a volume that is occupied by the modifier molecules. The calculation unit 40 may be, for example, a calculation unit of a personal computer.

[Obtaining of Volume Occupied by Surface Material]

The calculation unit 40 obtains the volume magnetic susceptibilities of a first particle and a second particle in order to obtain a volume that is occupied by a surface material covering the surface of the particle p. The second particle is obtained by covering the first particle (the particle p) with the surface material. Therefore, the first particle has a surface that is not covered with surface material unlike the second particle.

The surface material is a highly adsorptive material, such as a nonionic surfactant, a cationic surfactant, an anionic surfactant, or the like. When a surfactant is used, one of a nonionic surfactant, a cationic surfactant, and an anionic surfactant is selected according to the properties of the surface of the first particle so that the entire surface of the first particle is covered with the surfactant. Note that the surface material is not particularly limited and may be any material that can cover the entire surface of the first particle. For example, the surface material may be modifier molecules that can cover the entire surface of the first particle.

Here, an overview of obtaining of a magnetophoretic velocity $v_p$ of the particle p by the particle analysis device 10 will be described with reference to FIG. 1. The calculation unit 40 obtains the magnetophoretic velocity $v_p$ of the particle p from the result of measurement by the measurement unit 30. For example, the calculation unit 40 may obtain the magnetophoretic velocity $v_p$ of the particle p from a change over time in position information indicating the position of the particle p measured by the measurement unit 30. As an example of this, the measurement unit 30 may capture an image of the particle p at predetermined time intervals, and the calculation unit 40 may obtain the magnetophoretic velocity $v_p$ of the particle p from the results of the image capturing. Thereafter, the calculation unit 40 obtains the volume magnetic susceptibility $\chi_p$ of the particle p from the magnetophoretic velocity $v_p$ of the particle p. The motion of the particle p is determined by the volume magnetic susceptibility $\chi_p$ of the particle p and the volume magnetic susceptibility $\chi_f$ of the dispersion medium f. Note that the volume magnetic susceptibility is a parameter that depends on an electron state, which is an index having high physical reliability. Thus, the particle analysis device 10 obtains the magnetophoretic velocity $v_p$ of the particle p.

Therefore, when the volume magnetic susceptibility of the first particle (the particle p) is obtained, a first dispersion system including a first dispersion medium f1 and at least one first particle p1 dispersed therein is prepared. When the volume magnetic susceptibility of the second particle is obtained, a second dispersion system including a second dispersion medium f2 and at least one particle p2 dispersed therein is prepared.

Figure 2:
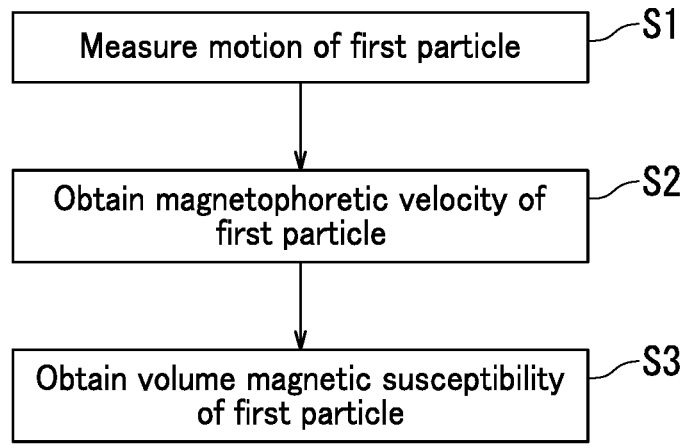
FIG. 2 is a diagram showing the flow of a process for obtaining the volume magnetic susceptibility of a first particle in an embodiment of the present invention.

Firstly, an operation of the particle analysis device 10 to obtain the volume magnetic susceptibility $\chi_p1$ of the first particle p1 will be described with reference to FIG. 2. FIG. 2 shows the flow of a process for obtaining the volume magnetic susceptibility $\chi_p1$ of the first particle p1. As shown in FIG. 2, initially, the measurement unit 30 measures the motion of the first particle p1 (step S1). Next, the calculation unit 40 obtains a magnetophoretic velocity $v_p1$ of the first particle p1 on the basis of the result of the measurement of the motion of the first particle p1 (step S2). Next, the calculation unit 40 obtains the volume magnetic susceptibility $\chi_p1$ of the first particle p1 (step S3).

Figure 3:
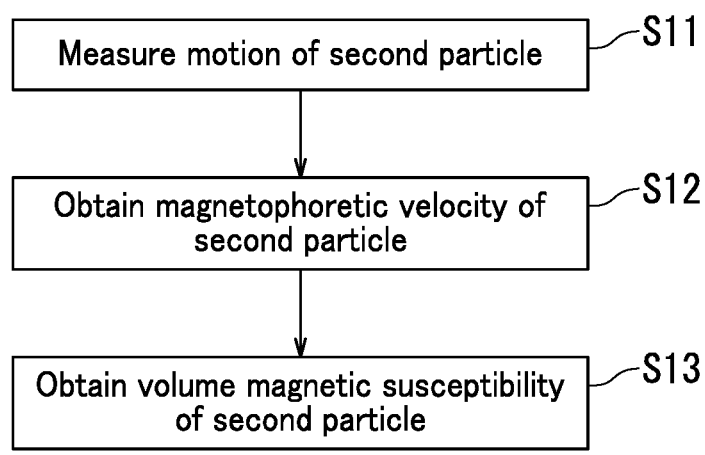
FIG. 3 is a diagram showing the flow of a process for obtaining the volume magnetic susceptibility of a second particle in an embodiment of the present invention.

Next, an operation of the particle analysis device 10 to obtain the volume magnetic susceptibility $\chi_p2$ of the second particle p2 will be described with reference to FIG. 3. FIG. 3 shows the flow of a process for obtaining the volume magnetic susceptibility $\chi_p2$ of the second particle p2. As shown in FIG. 3, initially, the measurement unit 30 measures the motion of the second particle p2 (step S11). Next, the calculation unit 40 obtains a magnetophoretic velocity $v_p2$ of the second particle p2 on the basis of the result of the measurement of the motion of the second particle p2 (step S12). Next, the calculation unit 40 obtains the volume magnetic susceptibility $\chi_p2$ of the second particle p2 (step S13). Although it is desirable that the second dispersion medium f2 be the same medium as the first dispersion medium f1, the second dispersion medium f2 may be different from the first dispersion medium f1.

Thereafter, the calculation unit 40 obtains a volume Vs that is occupied by a surface material s included in the second particle p2 on the basis of a relationship between the volume magnetic susceptibility $\chi_p1$ of the first particle p1, the volume Vp1 of the first particle p1, the volume magnetic susceptibility $\chi_p2$ of the second particle p2, the volume Vp2 of the second particle p2, the volume Vs that is occupied by the surface material s, and the volume magnetic susceptibility $\chi_s$ of the surface material s. The volume Vp1 of the first particle p1 may, for example, be obtained on the basis of the diameter of the first particle p1 calculated from a captured image of the first particle p1 in the first dispersion medium f1 on the assumption that the first particle p1 is in the shape of a sphere. Alternatively, the volume Vp1 of the first particle p1 may be obtained on the basis of the diameter of the first particle p1 that is a catalog value on the assumption that the first particle p1 is in the shape of a sphere. Alternatively, the volume Vp1 of the first particle p1 may be a catalog value thereof. The volume Vp2 of the second particle p2 may, for example, be obtained on the basis of the diameter of the second particle p2 calculated from a captured image of the second particle p2 in the second dispersion medium f2 on the assumption that the second particle p2 is in the shape of a sphere. The volume magnetic susceptibility $\chi_s$ of the surface material s can be estimated from the structural formula of the surface material s according to Pascal's law. Alternatively, the volume magnetic susceptibility $\chi_s$ of the surface material s can be actually measured in gram using a SQUID device, a magnetic balance, or the like.

When the volume magnetic susceptibility $\chi_p2$ of the second particle p2 is obtained, one second particle p2 may be arbitrarily selected from a plurality of the second particles p2 dispersed in the second dispersion medium f2, and the volume magnetic susceptibility $\chi_p2$ of the selected second particle p2 may be obtained. Alternatively, the average of these volume magnetic susceptibilities $\chi_p2$ may be obtained in a manner that a predetermined number of the second particles p2 are arbitrarily selected from the second particles p2 and the volume magnetic susceptibility $\chi_p2$ of each of the selected second particles p2 is obtained. Alternatively, the volume magnetic susceptibility $\chi_p2$ of each of all the second particles p2 may be obtained, and the average of these volume magnetic susceptibilities $\chi_p2$ may be obtained.

When the volume magnetic susceptibility $\chi_p1$ of the first particle p1 is obtained, the volume magnetic susceptibility $\chi_p1$ of the target first particle p1 is obtained. Through the above, the volume Vs that is occupied by the surface material s in an assumed situation where the surface of the target first particle p1 is covered with the surface material s, can be obtained. Therefore, the volume Vs that is occupied by the surface material s can be obtained for individual first particles p1. Alternatively, the volume Vs that is occupied by the surface material s in an assumed situation where the surface of the first particle p1 is covered with the surface material s may be obtained in a manner that a predetermined number of the first particles p1 are arbitrarily selected from the first particles p1; the volume magnetic susceptibility $\chi_p 1$ of each of the selected first particles p1 is obtained; and the average of these volume magnetic susceptibilities $\chi_p 1$ is obtained. Alternatively, the volume Vs that is occupied by the surface material s in an assumed situation where the surface of the first particle p1 is covered with the surface material s may be obtained in a manner that the volume magnetic susceptibility $\chi_p 1$ of each of all the first particles p1 is obtained and the average of these volume magnetic susceptibilities $\chi_p 1$ is obtained.

Note that the first particle p1 and the second particle p2 present in a dispersion medium may swell.

[Obtaining of Surface Area]

As described with reference to FIG. 4, the calculation unit 40 obtains the surface area of the first particle p1 after obtaining the volume Vs that is occupied by the surface material s. The surface area of the first particle p1 is obtained on the assumption that the surface material s forms a monolayer film on the entire surface of the first particle p1 with the molecules included in the surface material s having the closest packed structure.

Figure 4:
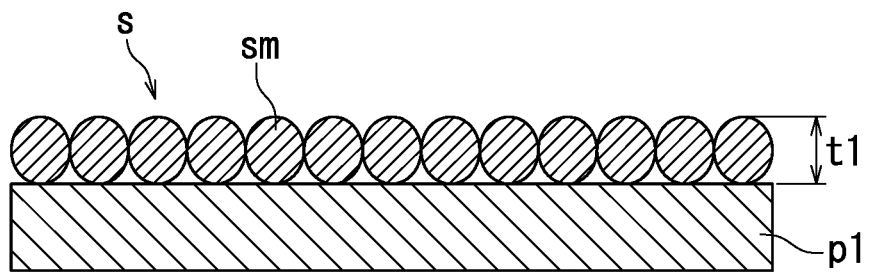
FIG. 4 is a schematic diagram in an assumed situation where the surface of a first particle is covered with a surface material in an embodiment of the present invention.

FIG. 4 is a schematic diagram showing a portion of the first particle p1 in an assumed situation where the surface of the first particle p1 is covered with the surface material s. In other words, FIG. 4 is a schematic enlarged cross-sectional view of a portion of a second particle p2.

As shown in FIG. 4, when it is assumed that the surface material s forms a monolayer film on the entire surface of the first particle p1 with the molecules (surface molecules) sm included in the surface material s having the closest packed structure, the surface area of the first particle p1 can be obtained by dividing the volume Vs that is occupied by the surface material s covering the entire surface of the first particle p1 by the molecular length t1 of the surface molecules sm. Therefore, the calculation unit 40 obtains the surface area of the first particle p1 by dividing the previously obtained volume Vs that is occupied by the surface material s by the molecular length t1 of the surface molecules sm. The molecular length t1 may be calculated using the van der Waals radius.

Note that, in order to increase accuracy of the value of the obtained surface area, surface areas may be measured using different surface materials, and the measured surface areas may be compared with each other. For example, in a situation where a cationic surfactant is used as a surface material, the surface areas may be measured using different cationic surfactants, and the measured surface areas may be compared with each other. Alternatively, the surface areas may be measured using different dispersion media, and the measured surface areas may be compared with each other.

[Obtaining of Pore Diameter]

As described with reference to FIGS. 5 and 6, when the first particle p1 (the particle p) is porous, the calculation unit 40 can also obtain the average diameter (pore diameter) of pores formed in the first particle p1.

Figure 5:
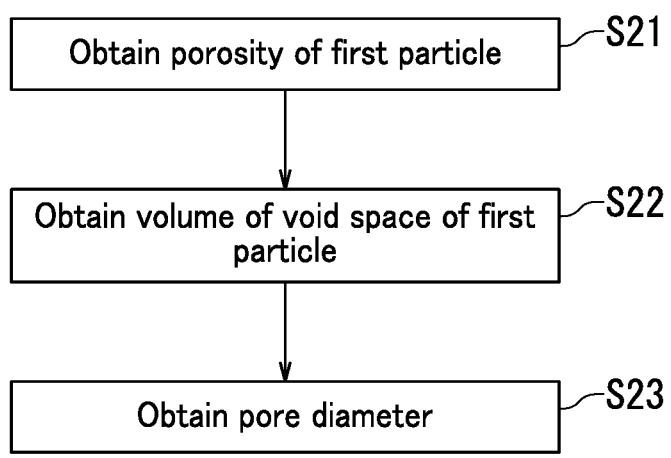
FIG. 5 is a diagram showing the flow of a process for obtaining a pore diameter in an embodiment of the present invention.

FIG. 5 shows the flow of a process for obtaining the pore diameter. When the pore diameter is obtained, the calculation unit 40 initially obtains the porosity of the first particle p1 on the basis of a relationship between the volume magnetic susceptibility $\chi_p 1$ of the first particle p1, the volume magnetic susceptibility $\chi_d 1$ of the body (substantial portion) of the first particle p1, and the volume magnetic susceptibility $\chi_f 1$ of the first dispersion medium f1, as shown in FIG. 5 (step S21). The volume magnetic susceptibility $\chi_p 1$ is the volume magnetic susceptibility of the first particle p1 where the first dispersion medium f1 infiltrates into the pores of the first particle p1. The volume magnetic susceptibility $\chi_d 1$ is the volume magnetic susceptibility of the body of the first particle p1 where the dispersion medium does not infiltrate into the pores of the first particle p1. For the volume magnetic susceptibility $\chi_d 1$ of the body of the first particle p1 and the volume magnetic susceptibility $\chi_f 1$ of the first dispersion medium f1, literature values are used. The particle analysis device 10 can directly obtain the porosity of the particle p from the motion of the particle p, i.e., can measure the porosities of individual particles p.

Next, as shown in FIG. 5, the calculation unit 40 obtains the volume Vpore of the void space of the first particle p1 on the basis of a relationship between the porosity of the first particle p1, the volume Vpore of the void space of the first particle p1, and the volume Vp1 of the first particle p1 (step S22). The value of the volume Vpore of the void space of the first particle p1 is the total value of the volumes of the pores formed in the first particle p1.

Next, as shown in FIG. 5, the calculation unit 40 obtains the pore diameter on the basis of the ratio between the volume Vpore of the void space of the first particle p1 and the surface area of the first particle p1 (step S23). When the first particle p1 is porous, it can be inferred that the surface area of the first particle p1 is equal to the total value of the areas of the inner surfaces of the pores formed in the first particle p1. Therefore, it is inferred that the ratio between the volume Vpore of the void space of the first particle p1 and the surface area of the first particle p1 is equal to the ratio (specific surface area) between the volume Vpore of the void space of the first particle p1 and the total value of the areas of the inner surfaces of the pores. In this embodiment, the pores are assumed to have the same cylindrical shape.

Figure 6:
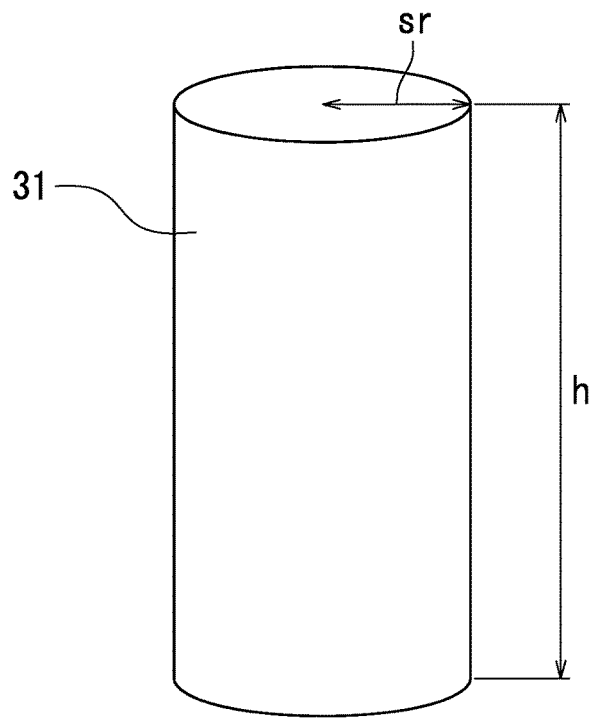
FIG. 6 is a schematic diagram showing a model cylindrical pore in an embodiment of the present invention.

FIG. 6 is a schematic diagram showing a model cylindrical pore 31. When the pore 31 is cylindrical, the ratio between the volume (the volume of the cylinder) $\alpha$ of the pore 31 and the area $\beta$ of the side surface of the cylinder is considered to be equal to the above specific surface area. Specifically, as shown in FIG. 6, the volume $\alpha$ of the pore 31 is "$\pi sr^2 h$," and the area $\beta$ of the side surface of the cylinder is "$2\pi rh$," where sr is the radius of the cylinder, and h is the height of the cylinder. The ratio "$\beta/\alpha$" between the volume $\alpha$ of the pore 31 and the area $\beta$ of the side surface of the cylinder is "$2/sr$." The ratio "$\beta/\alpha$" is considered to be equal to the value of the above specific surface area. Therefore, the pore diameter can be obtained. In this embodiment, the pore diameter (the average diameter of the pores) indicates a value that is obtained on the assumption that the pores 31 having the same cylindrical shape are uniformly distributed and present in the particle p.

Note that the porosity measured by the particle analysis device 10 is not simply determined only by the shape of the particle p, and indicates a relationship between the particle p and the dispersion medium f in which the particle p is present. For example, if the same particle p is dispersed in different dispersion media f, the particle p may have different porosity values. Therefore, the porosity can be used to find a state of the dispersion medium f infiltrating into the particle p.

[Obtaining of Pore Depth]

As described with reference to FIG. 7, the calculation unit 40 can also obtain the average depth of pores formed in the first particle p1. When the average depth of the pores is obtained, the calculation unit 40 obtains the average depth of the pores (pore depth) on the basis of a relationship between the volume Vpore of the void space of the first particle p1, the volume Vs that is occupied by the surface material s, the pore diameter (the average diameter of the pores), and the molecular length t1 of the surface molecules sm.

Figure 7:
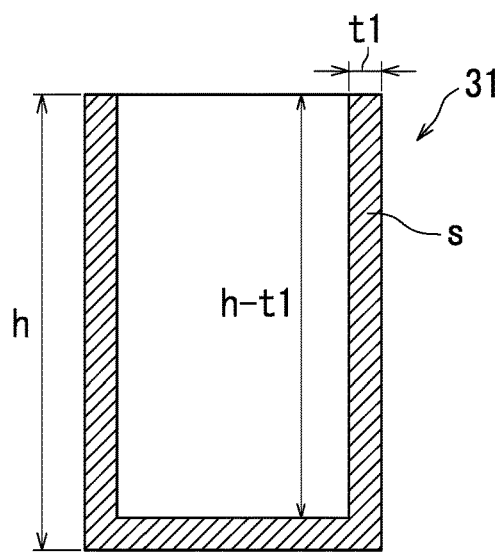
FIG. 7 is a schematic diagram of a pore in an assumed situation where the entire surface of a first particle is covered with a surface material in an embodiment of the present invention.

FIG. 7 is a schematic diagram of the pore 31 in an assumed situation where the entire surface of the first particle p1 is covered with the surface material s. In other words, FIG. 7 is a schematic cross-sectional view of the pore of the second particle p2. Here, as described above, it is assumed that the pores 31 have the same cylindrical shape. In other words, the average depth of the pores (pore depth) in this embodiment indicates a value that is obtained on the assumption that the pores 31 having the same cylindrical shape are uniformly distributed and present in the particle p.

As shown in FIG. 7, when the pore 31 is cylindrical, the inner surface of the cylinder is covered with the surface material s. The volume $\alpha 1$ of the pore 31 of the first particle p1 is "$\pi s r^2 h$" as described above. Therefore, when it is assumed that the entire surface of the first particle p1 is covered with the surface material s, the volume $\alpha 2$ of the pore 31, i.e., the volume of the pore of the second particle p2, is "$\pi (sr-t1)^2 (h-t1)$." Here, "t1" is the molecular length of the surface molecules sm included in the surface material s.

The volume $\alpha 3$ of the surface material s covering the inner surface of the pore 31 is calculated by "$\alpha 1 - \alpha 2$." Therefore, the ratio (volume ratio) $\alpha 3 / \alpha 1$ between the volume $\alpha 3$ of the surface material s covering the inner surface of the pore 31 and the volume $\alpha 1$ of the pore 31 of the first particle p1 is "$(\alpha 1 - \alpha 2)/\alpha 1$." When the pore 31 is cylindrical, the ratio Vs/Vpore between the volume Vs that is occupied by the surface material s and the volume Vpore of the void space of the first particle p1 is considered to be equal to the above volume ratio $\alpha 3/\alpha 1$, and therefore, the ratio Vs/Vpore and the ratio $\alpha 3/\alpha 1$ have a relationship represented by the following expression:

$$Vs/Vpore = (\alpha 1 - \alpha 2)/\alpha 1$$

In the above expression, the volume Vs that is occupied by the surface material s and the volume Vpore of the void space of the first particle p1 are already obtained. The pore diameter "2sr" is also already obtained. Therefore, the height h (pore depth) of the cylinder indicating the average depth of the pores can be obtained.

[Obtaining of Pore Volume]

The calculation unit 40 can also obtain the average volume of the pores. Here, as described above, it is assumed that the pores 31 have the same cylindrical shape. In other words, in this embodiment, the average volume of the pores (pore volume) indicates a value that is obtained on the assumption that the pores 31 having the same cylindrical shape are uniformly distributed and present in the particle p. When the average volume of the pores is obtained, the calculation unit 40 obtains the average volume of the pores (pore volume) on the basis of the pore diameter (the average diameter of the pores) and the pore depth (the average depth of the pores) h using an expression for obtaining the volume (the volume of a cylinder) $\alpha$ of the pore 31.

[Obtaining of Pore Number]

The calculation unit 40 can also obtain the number of pores formed in the first particle p1. When the number of the pores is obtained, the calculation unit 40 obtains the number of the pores (pore number) by dividing the volume Vpore of the void space of the first particle p1 by the pore volume (the average volume of the pores). Therefore, in this embodiment, the number of the pores (pore number) indicates a value that is obtained on the assumption that the pores 31 having the same cylindrical shape are uniformly distributed and present in the particle p.

[Obtaining of Surface Coverage Rate of Modifier Molecules]

The calculation unit 40 can also obtain the surface coverage rate of modifier molecules m. Prior to obtaining the surface coverage rate of the modifier molecules m, the calculation unit 40 obtains a volume Vm that is occupied by the modifier molecules m.

In order to obtain the volume Vm that is occupied by the modifier molecules m, a dispersion system including a dispersion medium fb and an unmodified particle pb present therein, and a dispersion system including a dispersion medium fa and a modified particle pa (i.e., the particle p) present therein, are prepared. Here, the unmodified particle pb corresponds to the above first particle p1; the modified particle pa corresponds to the above second particle p2; and the modifier molecules m correspond to the surface molecules sm included in the above surface material s. Therefore, the relationship between the unmodified particle pb, the modified particle pa, and the modifier molecules m is the same as that between the first particle p1, the second particle p2, and the surface molecules sm.

Therefore, as described with reference to FIGS. 8 and 9, the calculation unit 40 can obtain the volume magnetic susceptibilities of the unmodified particle pb and the modified particle pa in a manner similar to that in which the volume magnetic susceptibilities of the first particle p1 and the second particle p2 are obtained. The calculation unit 40 can also obtain the volume Vm that is occupied by the modifier molecules m in a manner similar to that in which the volume Vs that is occupied by the surface material s is obtained.

Note that the unmodified particle pb and the modified particle pa as present in the dispersion medium may swell. Although it is desirable that the dispersion medium fb and the dispersion medium fa be the same medium, the dispersion medium fb and the dispersion medium fa may be different media.

Figure 8:
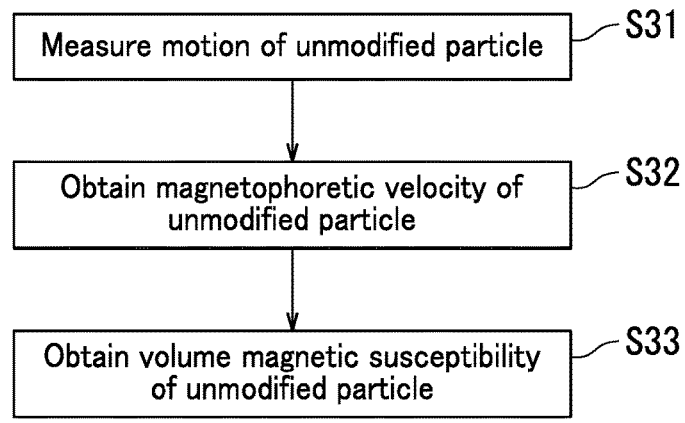
FIG. 8 is a diagram showing the flow of a process for obtaining the volume magnetic susceptibility of an unmodified particle in an embodiment of the present invention.

FIG. 8 shows the flow of a process for obtaining the volume magnetic susceptibility $\chi_p b$ of the unmodified particle pb. When the volume magnetic susceptibility $\chi_p b$ of the unmodified particle pb is obtained, initially the measurement unit 30 measures the motion of the unmodified particle pb as shown in FIG. 8 (step S31). Next, the calculation unit 40 obtains a magnetophoretic velocity $v_p b$ of the unmodified particle pb on the basis of the result of the measurement of the motion of the unmodified particle pb (step S32). Next, the calculation unit 40 obtains the volume magnetic susceptibility $\chi_p b$ of the unmodified particle pb (step S33).

Figure 9:
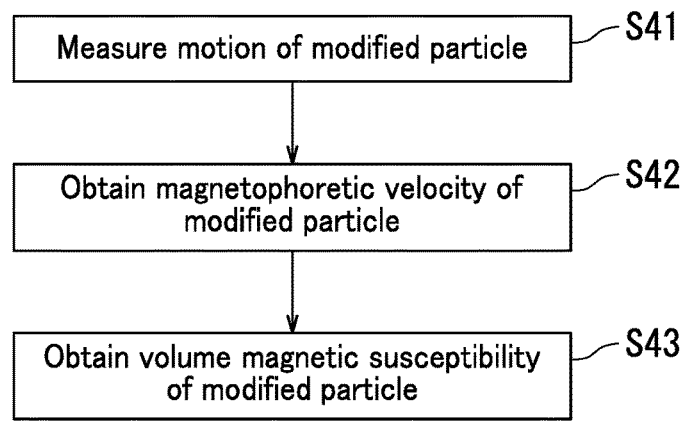
FIG. 9 is a diagram showing the flow of a process for obtaining the volume magnetic susceptibility of a modified particle in an embodiment of the present invention.

FIG. 9 shows the flow of a process for obtaining the volume magnetic susceptibility $\chi_p a$ of the modified particle pa. As shown in FIG. 9, initially, when the volume magnetic susceptibility $\chi_p a$ of the modified particle pa is obtained, the measurement unit 30 measures the motion of the modified particle pa (step S41). Next, the calculation unit 40 obtains a magnetophoretic velocity $v_p a$ of the modified particle pa on the basis of the result of the measurement of the motion of the modified particle pa (step S42). Next, the calculation unit 40 obtains the volume magnetic susceptibility $\chi_p a$ of the modified particle pa (step S43).

Thereafter, the calculation unit 40 obtains the volume Vm that is occupied by the modifier molecules m included in the modified particle pa, on the basis of a relationship between the volume magnetic susceptibility $\chi_p b$ of the unmodified particle pb, the volume Vpb of the unmodified particle pb, the volume magnetic susceptibility $\chi_p$a of the modified particle pa, the volume Vpa of the modified particle pa, the volume Vm that is occupied by the modifier molecules m, and the volume magnetic susceptibility $\chi_m$ of the modifier molecules m. The volume magnetic susceptibility $\chi_m$ of the modifier molecules m can be estimated from the structural formula of the modifier molecules m according to Pascal's law. Alternatively, the volume magnetic susceptibility $\chi_m$ of the modifier molecules m can be actually measured in gram using a SQUID device, a magnetic balance, or the like.

After obtaining the volume Vm that is occupied by the modifier molecules m, the calculation unit 40 obtains the number of the modifier molecules m included in the modified particle pa on the basis of the volume Vm that is occupied by the modifier molecules m, the density dm of the modifier molecules m, the molecular weight M. W of the modifier molecules m, and the Avogadro constant Na. As the density dm of the modifier molecules m, the density of sample modifier molecules m used for modifying particles is employed. The modifier molecules m are put on the surface of each of the particles at the same density as that of the sample. The product of the volume Vm that is occupied by the modifier molecules m and the density dm of the modifier molecules m indicates the mass of the modifier molecules m included in the modified particle pa. The value of the product of a value obtained by dividing the mass of the modifier molecules m by the molecular weight M. W of the modifier molecules m, and the Avogadro constant Na, indicates the number of the modifier molecules m.

Figure 10:
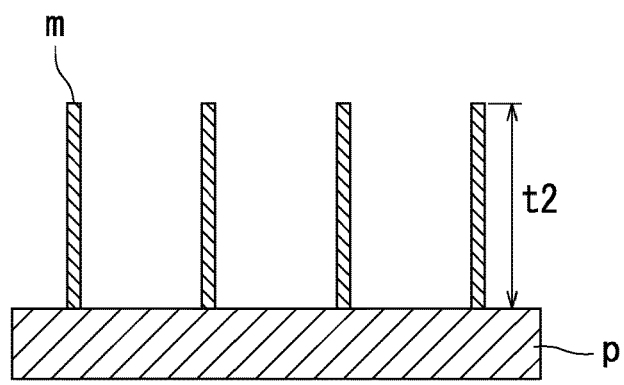
FIG. 10 is a schematic diagram of modifier molecules in an embodiment of the present invention.

Next, the calculation unit 40 obtains an area that is occupied by the modifier molecules m on the basis of the number of the modifier molecules m and the cross-sectional area Sm of each of the modifier molecules m, and obtains the proportion of the area that is occupied by the modifier molecules m to the surface area Sb of the unmodified particle pb (the surface coverage rate of the modifier molecules). This obtained value is equal to the surface coverage rate of the modifier molecules in the modified particle pa. FIG. 10 is a schematic diagram of the modifier molecules m put on the surface of the particle p, showing a portion of the particle p. As shown in FIG. 10, the modifier molecules m are provided in a standing position on the surface of the particle p. Therefore, the value of the product of the number of the modifier molecules m and the cross-sectional area Sm of each of the modifier molecules m indicates an area that is occupied by the modifier molecules m. The cross-sectional area Sm of each of the modifier molecules m can be calculated from the van der Waals radius. Also, the surface area Sb of the unmodified particle pb can be obtained in a manner similar to that in which the surface area of the first particle p1 is obtained.

As described above, the particle analysis device of this embodiment can be used to obtain information about the inside and surface of the particle p without destroying the particle p. Also, the particle analysis device of this embodiment can be used to analyze the uniformity of a plurality of particles p dispersed in the dispersion medium f.

A particle analysis method according to this embodiment will now be described.

[Method of Measuring Volume Magnetic Susceptibility]

Figure 11A:
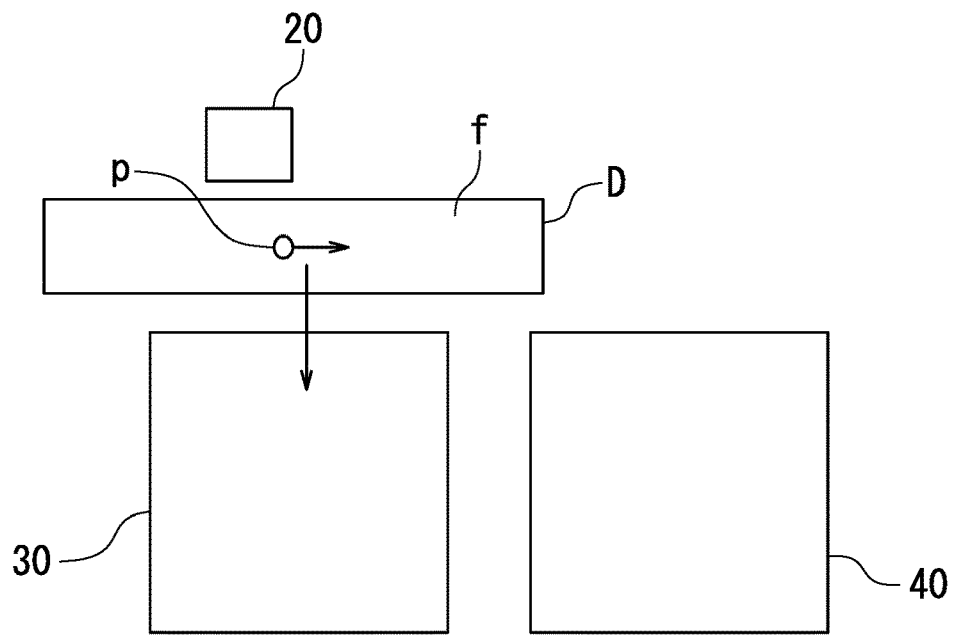
FIGS. 11A and 11B are schematic diagrams for describing a particle analysis method according to an embodiment of the present invention.
Figure 11B:
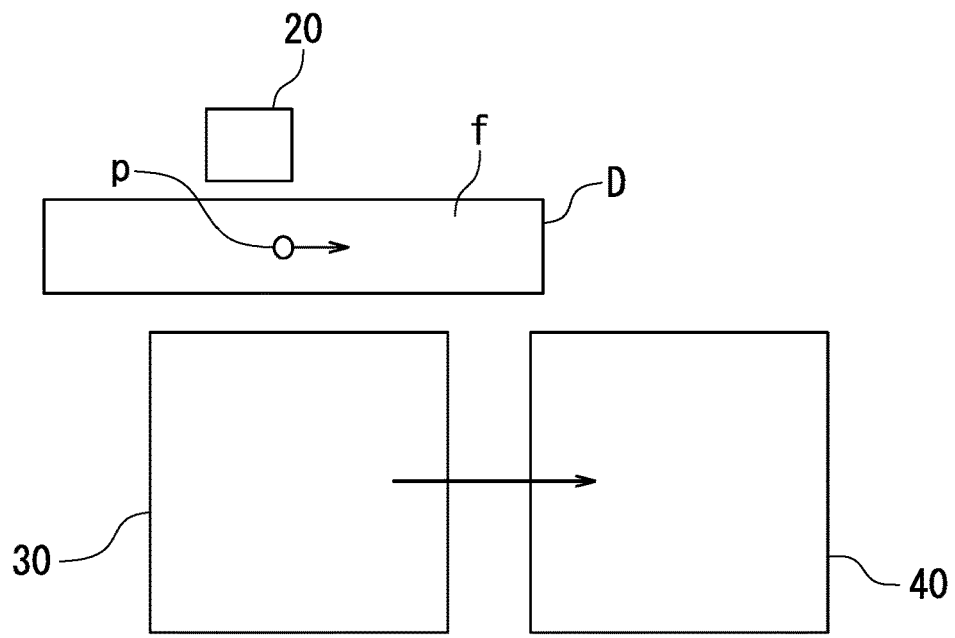

FIGS. 11A and 11B are schematic diagrams for describing the particle analysis method of this embodiment. A method of measuring the volume magnetic susceptibility $\chi_p$ of the particle p will be described with reference to FIGS. 11A and 11B.

Initially, as shown in FIG. 11A, the motion of the particle p in the dispersion medium f is measured in the presence of a magnetic field generated in the dispersion medium f.

Next, as shown in FIG. 11B, the magnetophoretic velocity $v_p$ of the particle p is obtained from the result of measurement of the motion of the particle p, and the volume magnetic susceptibility $\chi_p$ of the particle p is obtained from the magnetophoretic velocity $v_p$ of the particle p.

Note that the particle p may be a magnetic particle used in ink toner. Alternatively, the particle p may be a material used in cosmetics (e.g., foundation) or a material used in a drug delivery system (DDS). Note that, as described above, the particle p may be a cell. When the particle p is a cell, the shape of the particle p may change over time.

Figure 12A:
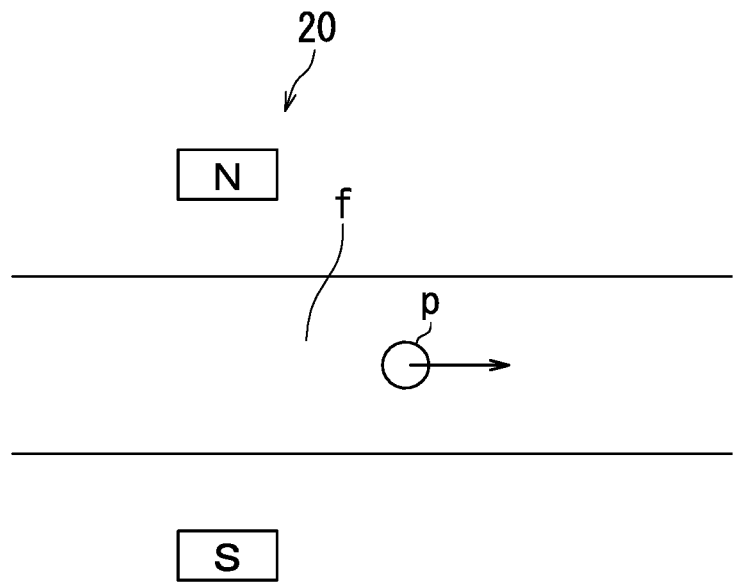
FIGS. 12A and 12B are schematic diagrams for describing a relationship between the volume magnetic susceptibility of a particle, the volume magnetic susceptibility of a dispersion medium, and the direction of movement of the particle in a particle analysis device according to an embodiment of the present invention.
Figure 12B:
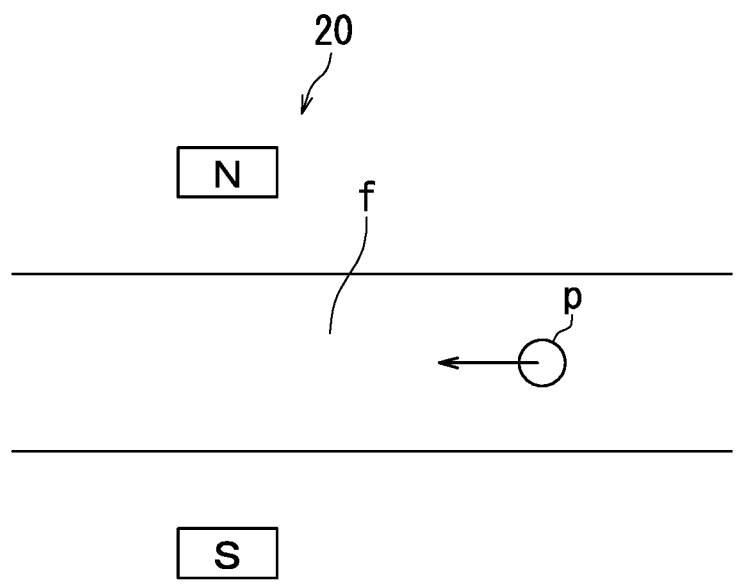

Here, the motion of the particle p will be described with reference to FIGS. 12A and 12B. FIGS. 12A and 12B are schematic diagrams for describing a relationship between the volume magnetic susceptibility of a particle, the volume magnetic susceptibility of a dispersion medium, and the direction of movement of the particle, in the particle analysis device of this embodiment. For example, the magnetic field generation unit 20 preferably generates a strong magnetic field and a large magnetic field gradient using a pole piece.

As shown in FIG. 12A, when the volume magnetic susceptibility $\chi_p$ of the particle p is smaller than the volume magnetic susceptibility $\chi_f$ of the dispersion medium f, the particle p moves in a direction away from the magnetic field. Note that the particle p receives a force in the vicinity of an end portion of a magnet (a superconducting magnet, a magnetic circuit, a permanent magnet, etc.). For example, the particle p receives a force within a distance of ±200 µm from the vicinity of the end portion of the magnet.

As shown in FIG. 12B, when the volume magnetic susceptibility $\chi_p$ of the particle p is greater than the volume magnetic susceptibility $\chi_f$ of the dispersion medium f, the particle p moves in a direction toward the magnetic field.

Figure 13:
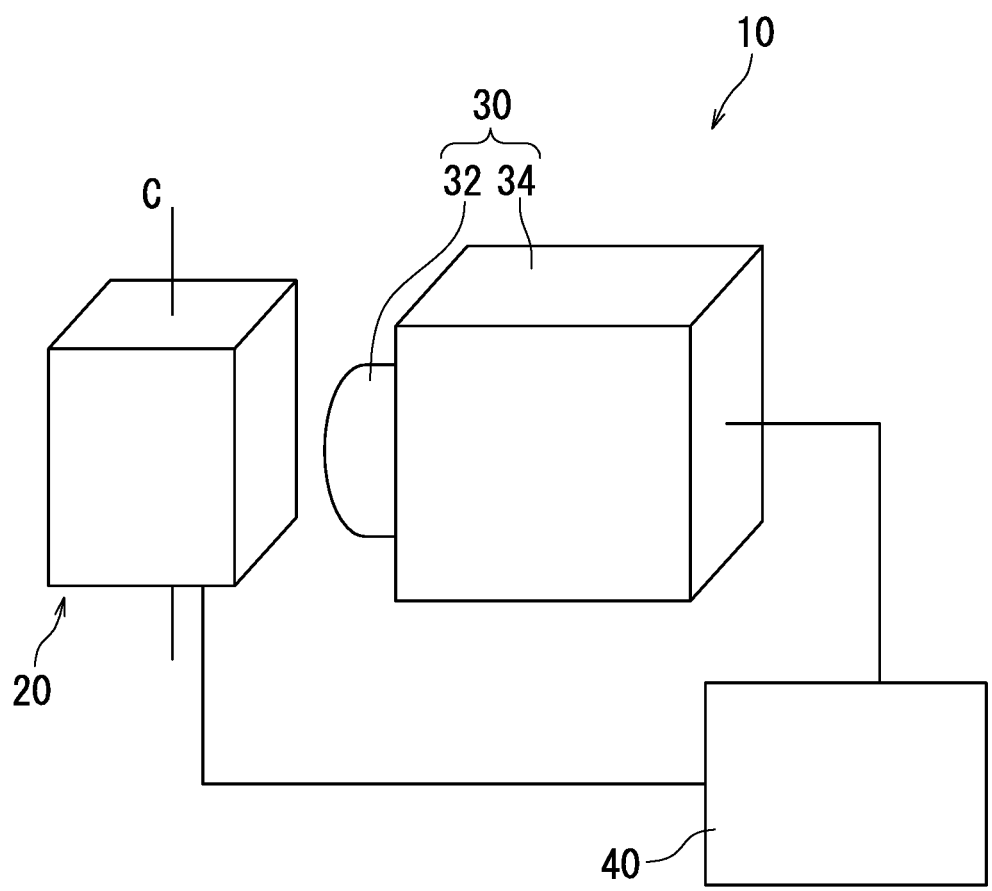
FIG. 13 is a schematic diagram of a particle analysis device according to an embodiment of the present invention.

FIG. 13 is a schematic diagram of the particle analysis device 10 of this embodiment. In the particle analysis device 10 shown in FIG. 13, a cell C containing the dispersion system D is provided in the vicinity of the magnetic field generation unit 20. For example, the cell C into which a solvent (solution) containing the particle p to be measured is introduced is a glass capillary, and a cross section of the cell C perpendicular to the axial direction of the capillary is in the shape of substantially a square of about 100 µm. At least one particle p as dispersed in a solvent is introduced into the capillary by means of capillary action or a pump.

The measurement unit 30 includes a magnification unit 32 and an image capture unit 34. For example, the magnification unit 32 includes an objective lens, and the image capture unit 34 includes a charge coupled device (CCD). The particle p is magnified by an appropriate factor by the magnification unit 32, and an image thereof is captured by the image capture unit 34. Note that the image capture unit 34 can typically measure not only the position of the particle p but also the diameter of the particle p. Therefore, the image capture unit 34 may measure the diameter of the particle p. Note that the image capture unit 34 may not measure the diameter of the particle p. For example, the image capture unit 34 may detect scattering light from the particle p to measure the position of the particle p.

The calculation unit 40 obtains the magnetophoretic velocity $v_p$ on the basis of the result of measurement performed by the measurement unit 30. The magnetophoretic velocity $v_p$ of the particle p is represented by the following expression (1).

[Math. 1]

$$v_p = \frac{2}{9} \frac{(\chi_p - \chi_f)r^2}{\eta \mu_0} B\left(\frac{dB}{dx}\right) \quad (1)$$

In Expression (1), $\chi_p$ is the volume magnetic susceptibility of the particle p, $\chi_f$ is the volume magnetic susceptibility of the dispersion medium f, r is the radius of the particle p, $\eta$ is the coefficient of viscosity of the dispersion medium f, $\mu_0$ is the magnetic permeability of vacuum, B is the magnetic flux density, and (dB/dx) is the gradient of the magnetic flux density. Note that Expression (1) is derived from the fact that the difference between a magnetic force applied to the particle p and a magnetic force applied to the dispersion medium f in the axial direction of the capillary (an example of the cell C) is substantially equal to the viscosity drag.

As described above, the magnetophoresis direction of the particle p is determined on the basis of the volume magnetic susceptibility $\chi_p$ of the particle p and the volume magnetic susceptibility $\chi_f$ of the dispersion medium f. Also, as can be seen from Expression (1), the magnetophoretic velocity $v_p$ of the particle p varies depending on the magnetic flux density B and/or the gradient (dB/dx) of the magnetic flux density.

The calculation unit 40 obtains the volume magnetic susceptibility $\chi_p$ of the particle p using the magnetophoretic velocity $v_p$ obtained from the result of the measurement performed by the measurement unit 30.

[Method of Measuring Surface Area of Particle]

In order to measure the surface area of the particle p, the first particle p1 that is the particle p, and in addition, the second particle p2 that is the particle p having a surface covered with the surface material s, are prepared as described above. The second particle p2 may, for example, be obtained by causing a surfactant to be adsorbed onto the surface of the particle p.

The calculation unit 40 obtains the volume magnetic susceptibility $\chi_p 1$ of the first particle p1 and the volume magnetic susceptibility $\chi_p 2$ of the second particle p2 using the above volume magnetic susceptibility measurement method.

Thereafter, the calculation unit 40 obtains the volume Vs that is occupied by the surface material s included in the second particle p2. The volume Vs corresponds to a volume that is occupied by the surface material s in an assumed situation where the first particle p1 is covered with the surface material s.

When the particle p is porous, the particle p has void space that is filled with the dispersion medium f, and the particle p is divided into the body (substantial portion) and the void space. Also, the product of the volume magnetic susceptibility and the volume has additive property. The value of the product of the volume magnetic susceptibility $\chi_p$ and the volume Vp of the particle p is equal to the total value of the products of the volume magnetic susceptibilities and the volumes of the respective components included in the particle p. Therefore, relationships represented by the following expressions (2) and (3) are established.

$$\chi_p 2 \times Vp2 = \chi_d 2 \times Vd2 + \chi_s \times Vs + \chi_{pore} 2 \times Vpore2 \quad (2)$$

$$\chi_p 1 \times Vp1 = \chi_d 1 \times Vd1 + \chi_{pore} 1 \times Vpore1 \quad (3)$$

In Expression (2), $\chi_p 2$ is the volume magnetic susceptibility of the second particle p2, Vp2 is the volume of the second particle p2, $\chi_d 2$ is the volume magnetic susceptibility of the body of the second particle p2, Vd2 is the volume of the body of the second particle p2, $\chi_s$ is the volume magnetic susceptibility of the surface material s, Vs is a volume that is occupied by the surface material s, $\chi_{pore} 2$ is the volume magnetic susceptibility of the void space of the second particle p2, and Vpore2 is the volume of the void space of the second particle p2. Also, in Expression (3), $\chi_p 1$ is the volume magnetic susceptibility of the first particle p1, Vp1 is the volume of the first particle p1, $\chi_d 1$ is the volume magnetic susceptibility of the body of the first particle p1, Vd1 is the volume of the body of the first particle p1, $\chi_{pore} 1$ is the volume magnetic susceptibility of the void space of the first particle p1, and Vpore1 is the volume of the void space of the first particle p1.

When the dispersion medium f1 of the first dispersion system and the dispersion medium f2 of the second dispersion system are the same medium, "$\chi_d 2 \times Vd2$" and "$\chi_d 1 \times Vd1$" are equal to each other in Expressions (2) and (3). Also, when the difference in volume of the void space (pore volume) between the first particle p1 and the second particle p2 is negligible, it can be assumed that "$\chi_{pore} 2 \times Vpore2$" and "$\chi_{pore} 1 \times Vpore1$" are equal to each other. Therefore, "Expression (2)–Expression (3)" results in a relationship represented by the following expression (4).

$$\chi_p 2 \times Vp2 - \chi_p 1 \times Vp1 = \chi_s \times Vs \quad (4)$$

Therefore, the calculation unit 40 can obtain the volume Vs that is occupied by the surface material s on the basis of the relationship between the volume magnetic susceptibility $\chi_p 1$ of the first particle p1, the volume Vp1 of the first particle p1, the volume magnetic susceptibility $\chi_p 2$ of the second particle p2, the volume Vp2 of the second particle p2, the volume Vs that is occupied by the surface material s included in the second particle p2, and the volume magnetic susceptibility $\chi_s$ of the surface material s. The volume magnetic susceptibility $\chi_s$ of the surface material s can be estimated from the structural formula of the surface material s according to Pascal's law. Alternatively, the volume magnetic susceptibility $\chi_s$ of the surface material s can be actually measured in gram using a SQUID device, a magnetic balance, or the like.

Figure 14:
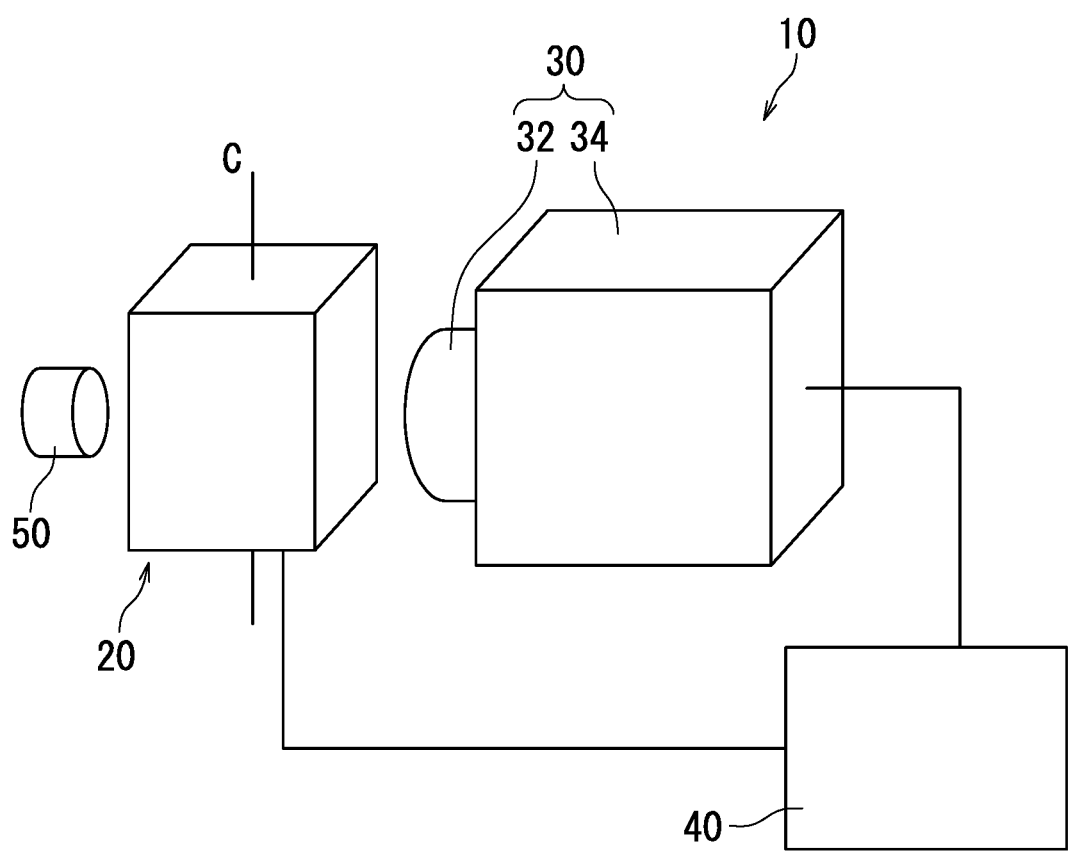
FIG. 14 is a schematic diagram of another example (1) of a particle analysis device according to an embodiment of the present invention.

Note that, as the first particle p1, a material having a known size may be used. Alternatively, the diameter of the first particle p1 may be measured, and the volume Vp1 of the first particle p1 may be obtained on the assumption that the first particle p1 is in the shape of a sphere. For example, the diameter of the first particle p1 may be measured using the measurement unit 30. Note that when the measurement unit 30 directly measures the diameter of the first particle p1, the particle analysis device 10 preferably includes a light source 50 as shown in FIG. 14. The volume Vp2 of the second particle p2 may be obtained on the assumption that the second particle p2 is in the shape of a sphere through measurement of the diameter of the second particle p2.

Alternatively, the first particle p1 may be trapped in a space formed between a convex lens and a flat glass plate or between a flat glass plate and another flat glass plate so that the diameter of the first particle p1 is measured. In this case, the interference of light between the two optical members is utilized. Alternatively, the diameter of the first particle p1 may be measured by utilizing scattering light from the first particle p1 undergoing Brownian motion. The diameter of the second particle p2 can be similarly measured in a similar manner.

Figure 15:
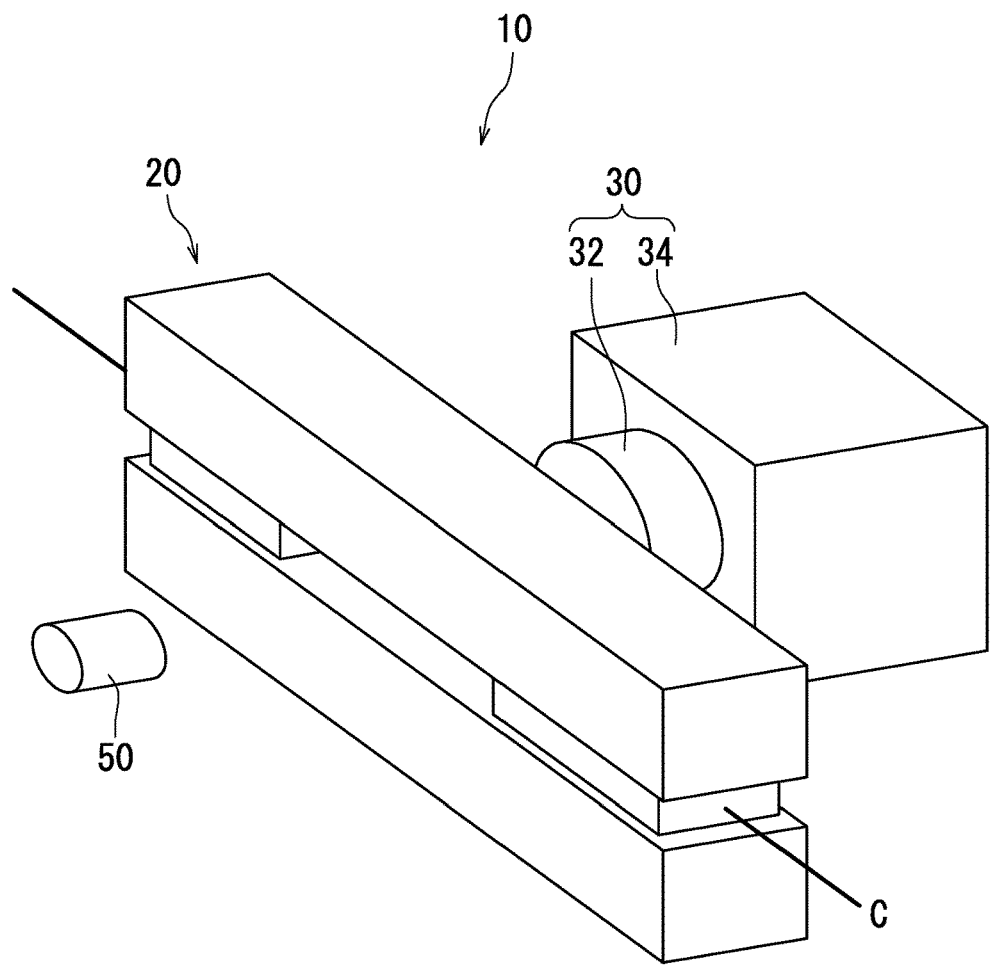
FIG. 15 is a schematic diagram of another example (2) of a particle analysis device according to an embodiment of the present invention.

Although, in the particle analysis device 10 shown in FIGS. 13 and 14, the capillary C into which the dispersion system D is introduced is placed in a vertical position, the present invention is not limited to this. As shown in FIG. 15, the capillary C may be placed in a horizontal position in the particle analysis device 10. For example, the magnetic field generation unit 20 generates a magnetic field having a magnetic flux density of 3 T.

After obtaining the volume Vs that is occupied by the surface material s, the calculation unit 40 obtains an area that is occupied by the molecules (surface molecules) sm included in the surface material s by dividing the volume Vs by the molecular length t1 of the surface molecules sm. The surface molecules sm cover the entire surface of the particle p (the first particle p1), and therefore, the area that is occupied by the surface molecules sm indicates the surface area of the particle p. This calculation is based on the assumption that the surface material s forms a monolayer film covering the entire surface of the particle p with the molecules sm included in the surface material s in the closest packed structure (see FIG. 4).

[Method of Measuring Porosity of Particle]

When the particle p is porous, the particle p has void space filled with the dispersion medium f, and the particle p is divided into the body (substantial portion) and the void space. In this case, the porosity of the particle p is represented by the following expression (5).

$$\text{Porosity} = V\text{pore}/Vp = V\text{pore}/(Vd + V\text{pore}) \tag{5}$$

In Expression (5), Vp is the volume of the particle p, Vd is the volume of the body of the particle p, and Vpore is the volume of the void space of the particle p.

Also, as can be seen from Expression (5), the volume Vp of the particle p is represented by the sum of the volume Vd of the body and the volume Vpore of the void space of the particle p. Specifically, a relationship represented by the following expression (6) is established.

$$Vp = Vd + V\text{pore} \tag{6}$$

Also, the product of the volume magnetic susceptibility and the volume has additive property. The value of the product of the volume magnetic susceptibility $\chi_p$ and the volume Vp of the particle p is equal to the total value of the products of the volume magnetic susceptibilities and the volumes of the respective components included in the particle p. Therefore, the value of the product of the volume magnetic susceptibility $\chi_p$ and the volume Vp of the particle p is equal to the total value of the product of the volume magnetic susceptibility $\chi_d$ and the volume Vd of the body of the particle p and the product of the volume magnetic susceptibility $\chi_{pore}$ and the volume Vpore of the void space of the particle p. Specifically, a relationship represented by the following expression (7) is established.

$$\chi_p V p = \chi_d V_d + \chi_{pore} V_{pore} \tag{7}$$

Therefore, a relationship represented by the following expression (8) is established according to Expressions (5), (6), and (7).

$$\begin{aligned}\text{Porosity} &= V\text{pore}/(Vd + V\text{pore}) \\ &= V\text{pore}/Vp \\ &= (\chi_p - \chi_d)/(\chi_{pore} - \chi_d)\end{aligned} \tag{8}$$

When the void space of the particle p is filled with the dispersion medium f, the volume magnetic susceptibility $\chi_{pore}$ of the void space of the particle p is equal to the volume magnetic susceptibility $\chi_f$ of the dispersion medium f, and therefore, Expression (8) can be rewritten as the following expression (9).

$$\text{Porosity} = (\chi_p - \chi_d)/(\chi_f - \chi_d) \tag{9}$$

As the volume magnetic susceptibility $\chi_d$ of the body of the particle p and the volume magnetic susceptibility $\chi_f$ of the dispersion medium f, literature values are used. Therefore, when the volume magnetic susceptibility $\chi_p$ of the particle p is measured, the calculation unit 40 can obtain the porosity of the particle p on the basis of the relationship represented by Expression (9) between the volume magnetic susceptibility $\chi_p$ of the particle p, the volume magnetic susceptibility $\chi_d$ of the body of the particle p, and the volume magnetic susceptibility $\chi_f$ of the dispersion medium f.

[Method of Measuring Volume of Void Space of Particle p]

According to Expression (5), when the porosity is measured, the volume Vpore of the void space of the particle p can be obtained. Specifically, the volume Vpore is represented by the following expression (10).

$$V\text{pore} = \text{porosity} \times Vp \tag{10}$$

Therefore, the calculation unit 40 can obtain the volume Vpore of the void space of the particle p on the basis of the relationship represented by Expression (10) between the volume Vpore of the void space of the particle p, the porosity of the particle p, and the volume Vp of the particle p.

[Method of Measuring Pore Diameter]

When the surface area of the particle p and the volume Vpore of the void space of the particle p are measured, the average diameter (pore diameter) of the pores formed in the particle p can be obtained. As described above, the average diameter of the pores indicates a value that is obtained on the assumption that pores having the same cylindrical shape are uniformly distributed and present in the particle p.

Specifically, when the particle p is porous, the surface area of the particle p can be estimated to be equal to the total value of the areas of the inner surfaces of the pores formed in the particle p. Therefore, the ratio between the volume Vpore of the void space of the particle p and the surface area of the particle p is estimated to be equal to the ratio (specific surface area) between the volume Vpore of the void space of the particle p and the total value of the areas of the inner surfaces of the pores. Meanwhile, when it is assumed that the pores have the same cylindrical shape, the volume (the volume of the cylinder) α of the pore is represented by the following expression (11), and the area β of the side surface of the cylinder is represented by the following expression (12), where sr is the radius of the pore (see FIG. 6).

$$\alpha = \pi sr^2 h \tag{11}$$

$$\beta = 2\pi sr h \tag{12}$$

Therefore, the ratio "β/α" between the volume α of the pore and the area β of the side surface of the cylinder is represented by the following expression (13).

$$\beta/\alpha = 2/sr \tag{13}$$

The ratio "β/α" represented by Expression (13) is considered to be equal to the value of the above specific surface area. Specifically, a relationship represented by the following expression (14) is established.

$$\beta/\alpha = \text{surface area of particle } p/V\text{pore} \tag{14}$$

Therefore, the radius sr is represented by the following expression (15).

$$sr = 2(V\text{pore/surface area of particle } p) \tag{15}$$

Because the pore diameter is "2sr," when the surface area of the particle p and the volume Vpore of the void space of the particle p are measured, the calculation unit 40 can obtain the pore diameter according to Expression (15).

[Method of Measuring Pore Depth]

Assuming that pores having the same cylindrical shape are uniformly distributed and present in the particle p, the average depth of the pores formed in the particle p is obtained. In other words, as described above, the average depth of pores (pore depth) indicates a value that is obtained on the assumption that pores having the same cylindrical shape are uniformly distributed and present in the particle p.

Specifically, when it is assumed that the pores have the same cylindrical shape, the volume (the volume of the cylinder) α1 of the pore before the entire surface of the particle p is covered with the surface material s, is represented by the following expression (16) (see FIG. 6).

$$\alpha 1 = \pi sr^2 h \tag{16}$$

Meanwhile, the volume (the volume of the cylinder) α2 of the pore after the entire surface of the particle p is covered with the surface material s, can be represented by the following expression (17) (see FIG. 7).

$$\alpha 2 = \pi (sr - t1)^2 (h - t1) \tag{17}$$

In Expression (17), as described above, "t1" is the molecular length of the surface molecules sm included in the surface material s.

Therefore, the volume α3 of the surface material s covering the inner surface of the pore can be represented by the following expression (18).

$$\alpha 3 = \alpha 1 - \alpha 2 \tag{18}$$

Therefore, the ratio (volume ratio) α3/α1 between the volume α3 of the surface material s covering the inner surface of the pore and the volume α1 of the pore before the entire surface of the particle p is covered with the surface material s, can be represented by the following expression (19).

$$\alpha 3/\alpha 1 = (\alpha 1 - \alpha 2)/\alpha 1 \tag{19}$$

When the pore is cylindrical, the ratio Vs/Vpore between the volume Vs that is occupied by the surface material s and the volume Vpore of the void space of the first particle p1 is considered to be equal to the above volume ratio α3/α1. Therefore, a relationship represented by the following expression (20) is established.

$$Vs/V\text{pore} = (\alpha 1 - \alpha 2)/\alpha 1 \tag{20}$$

Each calculation of the volume Vs that is occupied by the surface material s and the volume Vpore of the void space of the first particle p1 is already described. Therefore, Vs/Vpore can be obtained. When Vs/Vpore is represented by "A," Expression (20) can be rewritten as the following expression (21).

$$A = (\alpha 1 - \alpha 2)/\alpha 1 \tag{21}$$

Therefore, a relationship represented by the following expression (22) is established according to Expression (16), Expression (17), and Expression (21).

[Math. 2]

$$A = \frac{\pi sr^2 h - \pi (sr - t1)^2 (h - t1)}{\pi sr^2 h} \tag{22}$$

The height h of the cylinder indicating the average depth of the pores can be obtained by the following expression (23) according to Expression (22).

[Math. 3]

$$h = \frac{(sr - t1)^2 t1}{sr^2(A - 1) + (sr - t1)^2} \tag{23}$$

Therefore, the calculation unit 40 can obtain the average depth (pore depth) of the pores formed in the particle p on the basis of the relationship between the volume Vpore of the void space of the particle p, the volume Vs that is occupied by the surface material s, the pore diameter, and the molecular length t1 of the surface molecules sm.

[Method of Measuring Pore Volume]

Assuming that pores having the same cylindrical shape are uniformly distributed and present in the particle p, the average volume of the pores formed in the particle p is obtained. In other words, as described above, the average volume of the pores (pore volume) indicates a value that is obtained on the assumption that pores having the same cylindrical shape are uniformly distributed and present in the particle p.

Specifically, when it is assumed that the pores have the same cylindrical shape, the volume of the pore can be calculated by "$\pi sr^2 h$." Therefore, when the pore diameter (the average diameter of the pores) and the pore depth (the average depth of the pores) are obtained, the calculation unit 40 can obtain the average volume of the pores (pore volume).

[Method of Measuring Pore Number]

The number of the pores can be obtained by dividing the volume Vpore of the void space of the particle p by the pore volume (the average volume of the pores). Therefore, when the pore volume is obtained, the calculation unit 40 can obtain the number of the pores (pore number). As described above, in this embodiment, the number of the pores (pore number) indicates a value that is obtained on the assumption that pores having the same cylindrical shape are uniformly distributed and present in the particle p.

[Method of Measuring Surface Coverage Rate of Modifier Molecules]

When the surface of the particle p is modified by the modifier molecules m, the particle analysis device 10 of this embodiment can obtain the proportion of the modifier molecules m modifying the surface of the particle p (the surface coverage rate of the modifier molecules). Prior to obtaining the surface coverage rate of the modifier molecules m, the calculation unit 40 obtains the volume Vm that is occupied by the modifier molecules m.

In order to obtain the volume Vm that is occupied by the modifier molecules m, a dispersion system including a dispersion medium fb and an unmodified particle pb present therein and a dispersion system including a dispersion medium fa and a particle p, i.e., a modified particle pa, present therein, are prepared. The particle analysis device 10 of this embodiment obtains the volume magnetic susceptibility $\chi_p b$ of the unmodified particle pb and the volume magnetic susceptibility $\chi_p a$ of the modified particle pa using the above method of measuring the volume magnetic susceptibility.

Thereafter, the calculation unit 40 obtains the volume Vm that is occupied by the modifier molecules m in the modified particle pa. As described above, when the particle is porous, the particle has void space filled with the dispersion medium, and the particle is divided into the body (substantial portion) and the void space. Also, the product of the volume magnetic susceptibility and the volume has additive property. The value of the product of the volume magnetic susceptibility and the volume of a particle is equal to the total value of the products of the volume magnetic susceptibilities and the volumes of the respective components included in the particle. Therefore, relationships represented by the following expressions (24) and (25) are established.

$$\chi_p a \times Vpa = \chi_d a \times Vda + \chi_m \times Vm + \chi_{pore} a \times Vporea \quad (24)$$

$$\chi_p b \times Vpb = \chi_d b \times Vdb + \chi_{pore} b \times Vporeb \quad (25)$$

In Expression (24), $\chi_p a$ is the volume magnetic susceptibility of the modified particle pa, Vpa is the volume of the modified particle pa, $\chi_d a$ is the volume magnetic susceptibility of the body of the modified particle pa, Vda is the volume of the body of the modified particle pa, $\chi_m$ is the volume magnetic susceptibility of the modifier molecules m, Vm is a volume that is occupied by the modifier molecules m, $\chi_{pore} a$ is the volume magnetic susceptibility of the void space of the modified particle pa, and Vporea is the volume of the void space of the modified particle pa. Also, in Expression (25), $\chi_p b$ is the volume magnetic susceptibility of the unmodified particle pb, Vpb is the volume of the unmodified particle pb, $\chi_d b$ is the volume magnetic susceptibility of the body of the unmodified particle pb, Vdb is the volume of the body of the unmodified particle pb, $\chi_{pore} b$ is the volume magnetic susceptibility of the void space of the unmodified particle pb, and Vporeb is the volume of the void space of the unmodified particle pb.

When the dispersion medium fb of the dispersion system in which the unmodified particle pb is present is the same medium as the dispersion medium fa of the dispersion system in which the modified particle pa is present, "$\chi_d a \times Vda$" and "$\chi_d b \times Vdb$" are equal to each other in Expressions (24) and (25). Also, when a change in the volume of the void space (the total value of the volumes of the pores) between before and after the modification is negligible, "$\chi_{pore} a \times Vporea$" and "$\chi_{pore} b \times Vporeb$" can be defined as being equal to each other. Therefore, a relationship represented by the following expression (26) is established according to "Expression (24)-Expression (25)."

$$\chi_p a \times Vpa - \chi_p b \times Vpb = \chi_m \times Vm \quad (26)$$

Therefore, the calculation unit 40 can obtain the volume Vm that is occupied by the modifier molecules m on the basis of the relationship between the volume magnetic susceptibility $\chi_p a$ of the modified particle pa, the volume Vpa of the modified particle pa, the volume magnetic susceptibility $\chi_p b$ of the unmodified particle pb, the volume Vpb of the unmodified particle pb, the volume Vm that is occupied by the modifier molecules m, and the volume magnetic susceptibility $\chi_m$ of the modifier molecules m. The volume magnetic susceptibility $\chi_m$ of the modifier molecules m can be estimated from the structural formula of the modifier molecules m according to Pascal's law. Alternatively, the volume magnetic susceptibility $\chi_m$ of the modifier molecules m can be actually measured in gram using a SQUID device, a magnetic balance, or the like.

After obtaining the volume Vm that is occupied by the modifier molecules m, the calculation unit 40 obtains the number of the modifier molecules m (molecule number n) included in the modified particle pa according to the following expression (27).

$$n = Vm \times dm \times (1/M.W) \times Na \quad (27)$$

In Expression (27), Vm is a volume that is occupied by the modifier molecules m, dm is the density of the modifier molecules m, M. W is the molecular weight of the modifier molecules m, and Na is the Avogadro constant. Also, in Expression (27), the product of the volume Vm that is occupied by the modifier molecules m and the density dm of the modifier molecules m indicates the mass of the modifier molecules m included in the modified particle pa. A value obtained by dividing the mass of the modifier molecules m by the molecular weight M. W of the modifier molecules m indicates the mole number of the modifier molecules m. Therefore, the value of the product of the mole number of the modifier molecules m and the Avogadro constant Na is the number of the modifier molecules m (molecule number n). Note that, as the density dm of the modifier molecules m, the density of a sample of the modifier molecules m used for modifying the particle is employed. The modifier molecules m are put on the surface of the particle at the same density as that of this sample.

Next, the calculation unit 40 obtains the surface coverage rate of the modifier molecules m according to the following expression (28).

$$\text{Surface coverage rate} = n \times Sm \times (1/Sb) \times 100 \quad (28)$$

In Expression (28), Sm is the cross-sectional area of each of the modifier molecules m, and Sb is the surface area of the unmodified particle pb, i.e., the surface area of the particle pa (the particle p). Also, in Expression (28), the product of the molecule number n (the number of the modifier molecules m) and the cross-sectional area Sm of each of the modifier molecules m indicates an area that is occupied by the modifier molecules m. Therefore, by dividing the area that is occupied by the modifier molecules m by the surface area Sb of the unmodified particle pb, the proportion of the area that is occupied by the modifier molecules m to the surface area of the particle p (the surface coverage rate of the modifier molecules) can be obtained. As described above, the modifier molecules m are placed in a vertical position on the surface of the particle p (see FIG. 10). Therefore, the value of the product of the number of the modifier molecules m and the cross-sectional area Sm of each of the modifier molecules m indicates the area that is occupied by the modifier molecules m. The cross-sectional area Sm of each of the modifier molecules m can be calculated from the van der Waals radius. Also, the surface area Sb of the unmodified particle pb can be obtained using the above method of measuring the surface area of a particle.

Note that, in high performance liquid chromatography, which is frequently used for chemical analysis, silica gel particles each having a particle surface covered with a hydrophobic coating (straight-chain hydrocarbon octadecyl group) are typically used as a filler. High performance liquid chromatography is widely used in the fields of pharmaceutical products, foods, industrial products, public health, and the like. The particle analysis device 10 of this embodiment can be used to analyze silica gel (ODS) particles each having a particle surface hydrophobized by octadecyl modification.

For example, ODS particles were dispersed in acetone, and a surfactant Triton X-100 was used as the surface material s. The average volume magnetic susceptibility $\chi_p 1$ of the ODS particles before adsorption of the surfactant (a plurality of the first particles p1), and the average volume magnetic susceptibility $\chi_p 2$ of the ODS particles after adsorption of the surfactant (a plurality of the second particles p2), were measured. As a result, the average volume magnetic susceptibility $\chi_p 1$ was found to be "−9.40×10$^{-6}$," and the average volume magnetic susceptibility $\chi_p 2$ was found to be "−8.40×10$^{-6}$." Therefore, the amount of a change in average volume magnetic susceptibility between before and after adsorption of the surfactant was "1.00×10$^{-6}$." Note that, here, 2000 ODS particles were used in order to obtain the average volume magnetic susceptibility.

Thereafter, the volume Vs of the adsorbed surfactant (the volume that is occupied by the surfactant) was obtained using Expression (4), and as a result, the volume Vs of the adsorbed surfactant was found to be "3.82×10$^{-17}$ [m$^3$]." Therefore, the proportion of the volume Vs of the adsorbed surfactant to the volume of each of the ODS particles was 14.2%. Here, the average particle volume Vp1 of the ODS particles before adsorption of the surfactant (the first particles p1) and the average particle volume Vp2 of the ODS particles after adsorption of the surfactant (the second particles p2) were "2.68×10$^{-16}$ [m$^3$]," and the volume magnetic susceptibility $\chi_s$ of the surfactant was "−7.00×10$^{-6}$."

Next, the molecular length of the surfactant was calculated from the van der Waals radius, and the area where the surfactant is adsorbed was calculated from the volume (occupied volume) Vs of the adsorbed surfactant. Because the surfactant Triton X-100 has a molecular length of "1 nm," the adsorbed area per particle (the surface area of the ODS particle) was found to be "3.82×10$^{-8}$ [m$^2$]." Also, the specific surface area was found to be "2.38×10$^8$ [m]." Meanwhile, when nitrogen gas was adsorbed on ODS particles, and the volume of the void space of the ODS particle and the surface area of the ODS particle were obtained using the BET technique, the volume of the void space was found to be "1 [mlg$^{-1}$]," and the surface area was found to be "300 [m$^2$g$^{-1}$]." Therefore, by the BET technique, the specific surface area was found to be "3.00×10$^8$ [m]." This value is close to the specific surface area of "2.38×10$^8$ [m]" that was calculated by the technique of this embodiment. Therefore, it is understood that the technique of this embodiment is effective.

Also, the volume of the void space of the ODS particle was found to be "1.60×10$^{-16}$ [m$^3$]." Meanwhile, as described above, the surface area of the ODS particle was found to be "3.82×10$^{-8}$ [m$^2$]." Therefore, according to Expression (15), the pore diameter was found to be "16 nm." In contrast to this, when nitrogen gas was adsorbed on ODS particles and the pore diameter was obtained using the BET technique, the pore diameter was found to be "14 nm." This value is close to the pore diameter of "16 nm" that was obtained using the technique of this embodiment. Therefore, it is understood that the technique of this embodiment is effective.

Also, the particle analysis device 10 of this embodiment can be used to analyze silica gel particles. For example, the surfactant Triton X-100 was used as the surface material s, and silica gel particles dispersed in acetone were analyzed. As a result, the average particle diameter and the average volume magnetic susceptibility $\chi_p 1$ of the silica gel particles before adsorption of the surfactant were found to be "5.81 μm" and "−9.36×10$^{-6}$," respectively, and the volume Vpore of the void space thereof was found to be "6.17×10$^{-17}$ [m$^3$]." Meanwhile, the average particle diameter and the average volume magnetic susceptibility $\chi_p 2$ of the silica gel particles after adsorption of the surfactant were found to be "5.62 μm" and "−8.92×10$^{-6}$," respectively, and the volume Vpore of the void space thereof was found to be "6.25×10$^{-17}$ [m$^3$]." Assuming that the silica gel particles had a spherical shape, the volume Vs of the adsorbed surfactant was found to be "1.75×10$^{-17}$ [m$^3$]." Also, because the surfactant Triton X-100 has a molecular length of "1 nm," the pore diameter was found to be "13.3 nm." Also, the ratio A of the volume Vs of the adsorbed surfactant and the volume Vpore of the void space of the silica gel particle was found to be "0.283." As a result, the average depth h of pores was found to be "120 nm," the average volume of the pores was found to be "1.68×10$^{-23}$ [m$^3$]," and the number of the pores was found to be "3.68×10$^7$."

Also, the particle analysis device 10 of this embodiment can be used to measure the surface coverage rate of octadecyl groups on the ODS particle. In this case, silica gel particles before surface treatment were the unmodified particle pb (object to be compared), and the average volume magnetic susceptibility $\chi_p b$ of the silica gel particles (object to be compared) containing a solvent (acetone) in pores thereof was found to be "−9.22×10$^{-6}$," and the volume magnetic susceptibility $\chi_m$ of the octadecyl group was found to be "−8.01×10$^{-6}$" from the molecular structure of the octadecyl group according to Pascal's law. Meanwhile, as described above, the average volume magnetic susceptibility $\chi_p a$ of the ODS particles was found to be "−9.40×10$^{-6}$." Here, the average particle volume Vpb of the unmodified silica gel particles and the average particle volume Vpa of the ODS particles were "2.68×10$^{-16}$ [m$^3$]," and the density dm of the octadecyl groups was "9.60×10$^8$ [gm$^{-3}$]."

Because the molecular weight M. W of an octadecyl group is "256 [gmol$^{-1}$]," and the Avogadro constant Na is "6.02×10$^{23}$ [molecules/mol]," the molecule number n of octadecyl groups per particle is found to be "1.37×10$^{19}$." In addition, because it is calculated from the van der Waals radius that the cross-sectional area Sm of an octadecyl group is "1.12×10$^{-8}$ [m$^2$]," and as described above, the surface area of an ODS particle is "3.82×10$^{-8}$ [m$^2$]," the surface coverage rate of octadecyl groups per particle was found to be "29.3%." In contrast to this, the surface coverage rate of octadecyl groups that was calculated by comparing the amount of the octadecyl groups used for modifying particle surfaces with the amount of the octadecyl groups left as residue, was "26%." This value is close to the surface coverage rate of "29.3%" that was obtained using the technique of this embodiment. Therefore, it is understood that the technique of this embodiment is effective.

As described above, according to this embodiment, the surface areas, the pore diameters (the average diameter of pores), and the like of individual particles can be measured. Moreover, according to this embodiment, when the surface of a particle is modified, the surface coverage rate of modifier molecules can be measured. Therefore, according to this embodiment, variations in characteristics of particles can be evaluated, and therefore, variations between products or variations between lots of products can be reduced. For example, the yield of particulate products, such as fillers for high performance liquid chromatography, adhesives, cosmetics, pharmaceutical products, and ink pigments, can be improved. In particular, according to this embodiment, the surface coverage rate can be measured for individual particles. Therefore, the quality of products including a particle whose surface has a function that plays a major role, such as adhesives, ink pigments, antibody-modified resins for separating a pharmaceutical product material, and the like, can be improved.

Figure 16:
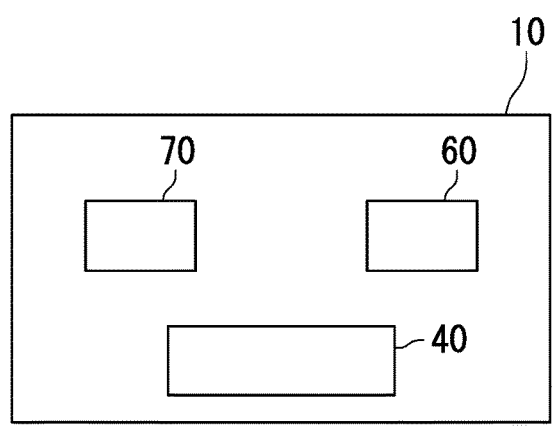
FIG. 16 is a schematic diagram of another example (3) of a particle analysis device according to an embodiment of the present invention.

Although, the particle analysis device 10 in this embodiment has been described in which the volume magnetic susceptibility of a particle is obtained by measuring the motion of the particle undergoing magnetophoresis, the present invention is not limited to this. As shown in FIG. 16, the particle analysis device 10 may include a calculation unit 40 and an input unit 60. The input unit 60 may include a man-machine interface (MMI), a pointing device, or the like. Specifically, for example, the input unit 60 includes a mouse, a trackball, a trackpad, a joystick, a keyboard, a controller, or the like. In the particle analysis device 10 of FIG. 16, data indicating the volume magnetic susceptibility of a particle is input to the calculation unit 40 through the input unit 60. Moreover, the particle analysis device 10 may include a display unit 70. Display of a numerical value (the volume magnetic susceptibility of a particle) input through the input unit 60 on the display unit 70 can improve convenience. The display unit 70 may include, for example, a liquid crystal display. The particle analysis device 10 of FIG. 16 may, for example, be a personal computer.

Also, although, the volume magnetic susceptibility of a particle is obtained by measuring the motion of the particle undergoing magnetophoresis in this embodiment, the method of obtaining the volume magnetic susceptibility of a particle is not limited to this. The volume magnetic susceptibility of a particle may be obtained using a SQUID device (e.g., a magnetic property measurement system: model No. MPMS3, manufactured by Quantum Design Japan, Inc.), a magnetic balance (e.g., a magnetic balance: model No. MSB-AUTO, manufactured by Sherwood Scientific Ltd. (SSL)), or the like. The volume magnetic susceptibility of a particle that is obtained using a SQUID device, a magnetic balance, or the like, may be input to the calculation unit 40 through the input unit 60 in the particle analysis device 10 of FIG. 16. Alternatively, the volume magnetic susceptibility of a particle may be obtained from a literature value. The volume magnetic susceptibility of a particle obtained from a literature value may be input in a similar manner to the calculation unit 40 through the input unit 60 in the particle analysis device 10 of FIG. 16.

Also, although, the particle is a fine particle or a cell in this embodiment, the particle is not limited to these, and may, for example, be a plate-like material.

INDUSTRIAL APPLICABILITY

The present invention can achieve measurement of the surface area of a particle, the average diameter of pores formed in a particle, the surface coverage rate of modifier molecules, and the like for individual particles, and is applicable to production of nanoparticles for use in the fields of cosmetics, medical products, environment, and the like.

REFERENCE SIGNS LIST

10 PARTICLE ANALYSIS DEVICE
20 MAGNETIC FIELD GENERATION UNIT
30 PARTICLE MEASUREMENT UNIT
31 PORE
32 MAGNIFICATION UNIT
34 IMAGE CAPTURE UNIT
40 CALCULATION UNIT
50 LIGHT SOURCE
p PARTICLE
f DISPERSION MEDIUM
D DISPERSION SYSTEM
C CELL
s SURFACE MATERIAL
sm SURFACE MOLECULE
m MODIFIER MOLECULE

The invention claimed is:

1. A method for measuring characteristics of a particle, comprising: obtaining a volume magnetic susceptibility $xp1$ of a first particle by a computer, the first particle being porous; obtaining a volume magnetic susceptibility $xp2$ of a second particle by the computer, the second particle containing the first particle and surface molecules covering a surface of the first particle; obtaining a volume $Vp1$ of the first particle by the computer; obtaining a volume $Vp2$ of the second particle by the computer; obtaining a volume magnetic susceptibility $Xs$ of the surface molecules by the computer; obtaining a molecular length $t1$ of the surface molecules by the computer; calculating by the computer a volume $Vs$ occupied by the surface molecules on the basis of a relationship between the volume magnetic susceptibility $xp1$ of the first particle, the volume $Vp1$ of the first particle, the volume magnetic susceptibility $xp2$ of the second particle, the volume $Vp2$ of the second particle, the volume $Vs$ occupied by the surface molecules, and the volume magnetic susceptibility $Xs$ of the surface molecules; calculating by the computer a surface area of the first particle by dividing the volume $Vs$ occupied by the surface molecules by the molecular length $t1$ of the surface molecules; wherein the obtaining the volume magnetic susceptibility $xp1$ of the first particle by the computer includes: measuring by an image sensor a motion of the first particle in a first dispersion medium in the presence of a magnetic field generated in the first dispersion medium; calculating by the computer a magnetophoretic velocity of the first particle from a result of the measurement of the motion of the first particle; and calculating by the computer the volume magnetic susceptibility $xp1$ of the first particle from the magnetophoretic velocity of the first particle, and the obtaining the volume magnetic susceptibility $xp2$ of the second particle by the computer includes: measuring by the image sensor a motion of the second particle in a second dispersion medium in the presence of a magnetic field generated in the second dispersion medium; calculating by the computer a magnetophoretic velocity of the second particle from a result of the measurement of the motion of the second particle; and calculating by the computer the volume magnetic susceptibility $xp2$ of the second particle from the magnetophoretic velocity of the second particle.

2. The method for measuring characteristics of a particle according to claim 1, further comprising: obtaining a volume magnetic susceptibility $xd$ of a body of the first particle by the computer; obtaining a volume magnetic susceptibility $xf$ of the first dispersion medium by the computer; calculating by the computer a porosity of the first particle on the basis of the volume magnetic susceptibility $xp1$ of the first particle, the volume magnetic susceptibility $xd$ of the body of the first particle, and the volume magnetic susceptibility $xf$ of the first dispersion medium; calculating by the computer a volume $Vpore$ of a void space of the first particle on the basis of the porosity and the volume $Vp1$ of the first particle; calculating by the computer an average radius $sr$ of pores formed in the first particle on the basis of a relationship between the average radius $sr$ of the pores and a ratio between the volume $Vpore$ of the void space of the first particle and the surface area of the first particle; calculating by the computer an average diameter of the pores on the basis of the average radius $sr$ of the pores.

3. The method for measuring characteristics of a particle according to claim 2, further comprising: calculating by the computer an average depth h of the pores on the basis of the volume Vpore of the void space of the first particle, the volume Vs occupied by the surface molecules, the average radius sr of the pores, and the molecular length t1 of the surface molecules.

4. The method for measuring characteristics of a particle according to claim 3, further comprising: calculating by the computer an average volume of the pores on the basis of the average radius sr of the pores and the average depth h of the pores.

5. The method for measuring characteristics of a particle according to claim 4, further comprising: calculating by the computer a number of the pores formed in the first particle by dividing the volume Vpore of the void space of the first particle by the average volume of the pores.

6. The method for measuring characteristics of a particle according to claim 1, wherein the first dispersion medium and the second dispersion medium differ from each other.

7. A method for measuring characteristics of a particle, comprising: obtaining a volume magnetic susceptibility xpb of a first particle by a computer, the first particle being porous; obtaining a volume magnetic susceptibility xpa of a second particle by the computer, the second particle containing the first particle and modifier molecules covering the first particle; obtaining a volume Vpb of the first particle by the computer; obtaining a volume Vpa of the second particle by the computer; obtaining a volume magnetic susceptibility Xm of the modifier molecules by the computer; obtaining a density dm of the modifier molecules by the computer; obtaining a molecular weight M. W of the modifier molecules by the computer; obtaining the Avogadro constant Na by the computer; obtaining a cross-sectional area Sm of the modifier molecules by the computer; obtaining a molecular length of the modifier molecules by the computer; calculating by the computer a volume Vm occupied by the modifier molecules on the basis of a relationship between the volume magnetic susceptibility xpb of the first particle, the volume Vpb of the first particle, the volume magnetic susceptibility xpa of the second particle, the volume Vpa of the second particle, the volume Vm occupied by the modifier molecules, and the volume magnetic susceptibility xm of the modifier molecules; calculating by the computer a number n of the modifier molecules on the basis of the volume Vm occupied by the modifier molecules, the density dm of the modifier molecules, the molecular weight M. W of the modifier molecules, and the Avogadro constant Na; calculating by the computer a surface area Sb of the first particle by dividing the volume Vm occupied by the modifier molecules by the molecular length of the modifier molecules; calculating by the computer a surface coverage rate that indicates a proportion of an area occupied by the modifier molecules to the surface area Sb of the first particle on the basis of the number n of the modifier molecules, the cross-sectional area Sm of the modifier molecules, and the surface area Sb of the first particle; wherein the obtaining the volume magnetic susceptibility xpb of the first particle by the computer includes: measuring by an image sensor a motion of the first particle in a first dispersion medium in the presence of a magnetic field generated in the first dispersion medium; calculating by the computer a magnetophoretic velocity of the first particle from a result of the measurement of the motion of the first particle; and calculating by the computer the volume magnetic susceptibility xpb of the first particle from the magnetophoretic velocity of the first particle, and the obtaining the volume magnetic susceptibility xpa of the second particle by the computer includes: measuring by the image sensor a motion of the second particle in a second dispersion medium in the presence of a magnetic field generated in the second dispersion medium; calculating by the computer a magnetophoretic velocity of the second particle from a result of the measurement of the motion of the second particle; and calculating by the computer the volume magnetic susceptibility xpa of the second particle from the magnetophoretic velocity of the second particle.

8. A device for measuring characteristics of a particle, comprising: a computer; wherein the computer is configured to obtain a volume magnetic susceptibility xp1 of a first particle that is porous, obtain a volume magnetic susceptibility xp2 of a second particle that contains the first particle and surface molecules covering a surface of the first particle, obtain a volume Vp1 of the first particle, obtain a volume Vp2 of the second particle, obtain a volume magnetic susceptibility Xs of the surface molecules, obtain a molecular length t1 of the surface molecules, calculate a volume Vs occupied by the surface molecules on the basis of a relationship between the volume magnetic susceptibility xp1 of the first particle, the volume Vp1 of the first particle, the volume magnetic susceptibility xp2 of the second particle, the volume Vp2 of the second particle, the volume Vs occupied by the surface molecules, and the volume magnetic susceptibility Xs of the surface molecules, and calculate a surface area of the first particle by dividing the volume Vs occupied by the surface molecules by the molecular length t1 of the surface molecules, a magnetic field generation unit configured to generate a magnetic field; and an image sensor configured to measure a motion of a particle in a dispersion medium in the presence of the magnetic field generated by the magnetic field generation unit in the dispersion medium, wherein the image sensor measures a motion of the first particle in a first dispersion medium and a motion of the second particle in a second dispersion medium, and the computer is configured to calculate a magnetophoretic velocity of the first particle from a result of the measurement of the motion of the first particle, calculate the volume magnetic susceptibility xp1 of the first particle from the magnetophoretic velocity of the first particle, calculate a magnetophoretic velocity of the second particle from a result of the measurement of the motion of the second particle, and calculate the volume magnetic susceptibility xp2 of the second particle from the magnetophoretic velocity of the second particle.

9. The device for measuring characteristics of a particle according to claim 8, wherein the computer configured to obtain a volume magnetic susceptibility xd of a body of the first particle, obtain a volume magnetic susceptibility xf of the first dispersion medium, calculate a porosity of the first particle on the basis of the volume magnetic susceptibility xp1 of the first particle, the volume magnetic susceptibility xd of the body of the first particle, and the volume magnetic susceptibility xf of the first dispersion medium, calculate a volume Vpore of a void space of the first particle on the basis of the porosity and the volume Vp1 of the first particle, calculate an average radius sr of pores formed in the first particle on the basis of a relationship between the average radius sr of the pores and a ratio between the volume Vpore of the void space of the first particle and the surface area of the first particle, and calculate an average diameter of the pores on the basis of the average radius sr of the pores.

10. The device for measuring characteristics of a particle according to claim 9, wherein the computer configured to calculate an average depth h of the pores on the basis of the volume Vpore of the void space of the first particle, the volume Vs occupied by the surface molecules, the average radius sr of the pores, and the molecular length t1 of the surface molecules.

11. The device for measuring characteristics of a particle according to claim 10, wherein the computer configured to calculate an average volume of the pores on the basis of the average radius sr of the pores and the average depth h of the pores.

12. The device for measuring characteristics of a particle according to claim 11, wherein the computer configured to calculate a number of the pores formed in the first particle by dividing the volume Vpore of the void space of the first particle by the average volume of the pores.

13. The device for measuring characteristics of a particle according to claim 8, wherein the first dispersion medium and the second dispersion medium differ from each other.

14. A device for measuring characteristics of a particle, comprising: a computer; wherein the computer is configured to obtain a volume magnetic susceptibility xpb of a first particle that is porous, obtain a volume magnetic susceptibility xpa of a second particle that contains the first particle and modifier molecules covering a surface of the first particle, obtain a volume Vpb of the first particle, obtain a volume Vpa of the second particle, obtain a volume magnetic susceptibility xm of the modifier molecules, obtain a density dm of the modifier molecules, obtain a molecular weight M. W of the modifier molecules, obtain the Avogadro constant Na, obtain a cross-sectional area Sm of the modifier molecules, obtain a molecular length of the modifier molecules, calculate a volume Vm occupied by the modifier molecules on the basis of a relationship between the volume magnetic susceptibility xpb of the first particle, the volume Vpb of the first particle, the volume magnetic susceptibility xpa of the second particle, the volume Vpa of the second particle, the volume Vm occupied by the modifier molecules, and the volume magnetic susceptibility xm of the modifier molecules, calculate a number n of the modifier molecules on the basis of the volume Vm occupied by the modifier molecules, the density dm of the modifier molecules, the molecular weight M. W of the modifier molecules, and the Avogadro constant Na, calculate a surface area Sb of the first particle by dividing the volume Vm occupied by the modifier molecules by the molecular length of the modifier molecules, and calculate a surface coverage rate that indicates a proportion of an area occupied by the modifier molecules to the surface area Sb of the first particle on the basis of the number n of the modifier molecules, the cross-sectional area Sm of the modifier molecules, and the surface area Sb of the first particle; a magnetic field generation unit configured to generate a magnetic field; and an image sensor configured to measure a motion of a particle in a dispersion medium in the presence of the magnetic field generated by the magnetic field generation unit in the dispersion medium, wherein the image sensor measures a motion of the first particle in a first dispersion medium and a motion of the second particle in a second dispersion medium, and the computer calculates a magnetophoretic velocity of the first particle from a result of the measurement of the motion of the first particle, calculates the volume magnetic susceptibility xpb of the first particle from the magnetophoretic velocity of the first particle, calculates a magnetophoretic velocity of the second particle from a result of the measurement of the motion of the second particle, and calculates the volume magnetic susceptibility xpa of the second particle from the magnetophoretic velocity of the second particle.

* * * * *